United States Patent
Vanleeuwen et al.

(10) Patent No.: US 8,246,627 B2
(45) Date of Patent: Aug. 21, 2012

(54) CEMENT DELIVERY DEVICE FOR INTRODUCING CEMENT INTO TISSUE, THE DEVICE HAVING A CAVITY CREATOR

(75) Inventors: Ryan Vanleeuwen, Portage, MI (US); Frank J. Cinder, Scotts, MI (US); Jared P. Coffeen, Paw Paw, MI (US)

(73) Assignee: Stryker Corporation, Kalamazoo, MI (US)

( * ) Notice: Subject to any disclaimer, the term of this patent is extended or adjusted under 35 U.S.C. 154(b) by 938 days.

(21) Appl. No.: 12/187,727

(22) Filed: Aug. 7, 2008

(65) Prior Publication Data
US 2010/0036381 A1  Feb. 11, 2010

(51) Int. Cl.
*A61B 17/58* (2006.01)
*A61B 17/60* (2006.01)
*A61F 2/00* (2006.01)

(52) U.S. Cl. .......... 606/92; 606/79; 606/83; 606/93; 606/94

(58) Field of Classification Search .......... 606/92–94, 606/79–84
See application file for complete search history.

(56) References Cited

U.S. PATENT DOCUMENTS

| | | | |
|---|---|---|---|
| 4,969,888 A | 11/1990 | Scholten et al. |
| 5,015,255 A | 5/1991 | Kuslich |
| 5,059,193 A | 10/1991 | Kuslich |
| 5,062,845 A | 11/1991 | Kuslich et al. |
| 5,108,404 A | 4/1992 | Scholten et al. |
| 5,292,330 A | 3/1994 | Shutt |
| 5,390,683 A | 2/1995 | Pisharodi |
| 5,445,639 A | 8/1995 | Kuslich et al. |
| 5,549,679 A | 8/1996 | Kuslich |
| 5,928,239 A | 7/1999 | Mirza |
| 6,171,312 B1 | 1/2001 | Beaty |
| 6,224,604 B1 | 5/2001 | Suddaby |
| 6,383,188 B2 | 5/2002 | Kuslich et al. |
| 6,440,138 B1 | 8/2002 | Reiley et al. |
| 6,676,665 B2 | 1/2004 | Foley et al. |
| 6,679,886 B2 | 1/2004 | Weikel et al. |
| 6,746,451 B2 | 6/2004 | Middleton et al. |
| 6,814,734 B2 | 11/2004 | Chappuis et al. |
| 6,863,672 B2 | 3/2005 | Reiley et al. |
| 6,899,715 B1 | 5/2005 | Beaty |
| 6,981,981 B2 | 1/2006 | Reiley et al. |
| 7,097,648 B1 | 8/2006 | Globerman et al. |
| 7,114,501 B2 | 10/2006 | Johnson et al. |
| 7,160,306 B2 | 1/2007 | Matsuzaki et al. |
| 7,179,024 B2 | 2/2007 | Greenhalgh |
| 2004/0010315 A1 | 1/2004 | Song |
| 2004/0122457 A1 | 6/2004 | Weber |
| 2004/0133208 A1 | 7/2004 | Weikel et al. |
| 2004/0153064 A1 | 8/2004 | Foley et al. |
| 2005/0033303 A1 | 2/2005 | Chappuis et al. |
| 2005/0113836 A1 | 5/2005 | Lozier et al. |

(Continued)

FOREIGN PATENT DOCUMENTS

DE  39 22044 A1  2/1991

*Primary Examiner* — Andrew Yang

(57) ABSTRACT

A cavity creator including a tube with a lumen. A tip able to penetrate bone extends forward from the distal end of the tube. A blade is moveably attached to the outer tube proximal to the tip so as to move between retracted and extended states. The tube has a discharge port adjacent the blade. The tip is used to position the upper tube in bone. The blade is extended to form a cavity in the bone. Once the cavity is created filler material can be introduced into the cavity by flowing the material through the tube lumen.

28 Claims, 28 Drawing Sheets

U.S. PATENT DOCUMENTS

| | | |
|---|---|---|
| 2005/0182417 A1 | 8/2005 | Pagano |
| 2006/0116689 A1 | 6/2006 | Albans et al. |
| 2006/0116690 A1 | 6/2006 | Pagano |
| 2006/0224241 A1 | 10/2006 | Butler et al. |
| 2006/0235417 A1 | 10/2006 | Sala |
| 2007/0067034 A1 | 3/2007 | Chirico et al. |
| 2007/0123889 A1 | 5/2007 | Malandain et al. |
| 2007/0198013 A1 | 8/2007 | Foley et al. |
| 2007/0219634 A1 | 9/2007 | Greenhalgh et al. |
| 2008/0009875 A1 | 1/2008 | Sankaran et al. |
| 2008/0009876 A1 | 1/2008 | Sankaran et al. |
| 2008/0009877 A1 | 1/2008 | Sankaran et al. |
| 2008/0114364 A1 | 5/2008 | Goldin et al. |

CEMENT DELIVERY DEVICE FOR INTRODUCING CEMENT INTO TISSUE, THE DEVICE HAVING A CAVITY CREATOR

FIELD OF THE INVENTION

The present invention relates generally to a device for creating a cavity in bone. More particularly, the present invention is directed to a tool for creating a cavity within a vertebra or other bone and through which bone cement or other filler material can be percutaneously injected into the cavity to stabilize the bone.

BACKGROUND OF THE INVENTION

The spine, which forms the backbone of a person, consists of a number of individual bones known as vertebrae. A vertebra can be subjected to a compression fracture in which the normal shape of the bone becomes compressed and distorted. Compression fractures can occur as result of osteoporosis, a disease that results in a loss of normal bone density, mass. Trauma to the spine or other diseases can also cause compression fractures. The fracture of one or more vertebrae can result in extreme back pain. Other end effects of a vertebral fracture include decreased patient height and spinal deformity.

Vertebroplasty is a medical procedure in which bone cement is percutaneously injected into the fractured vertebra to stabilize the vertebra. The main goal of vertebroplasty is to reduce pain caused by the fracture(s) by stabilizing the bone. An undesirable side effect of vertbroplasty procedure is that the bone cement injected into a vertebra has been known to leak. This leaked cement can have undesirable effects on the other tissue and organs internal to the patient. To minimize this leakage, medical practitioners have been known to minimize as much as possible the volume of cement that is injected in the bone. This can result in too little cement being injected in the bone to have the desired therapeutic effect.

An alternative procedure for treating vertebral fractures that is related to vertebroplasty is kyphoplasty. A kyphoplasty procedure involves placement of a balloon into a collapsed vertebra, inflating the balloon to compress the cancellous tissue internal to the bone in order to create a void. Once the void is created, bone cement is injected into the void to stabilize the fracture. Many patients have experienced appreciable relief after undergoing a kyphoplasty procedure. However, when performing a kyphoplasty procedure, it can be difficult to control where within the vertebral bone the balloon inflates. This makes it difficult to control exactly where in the bone the void is created. Consequently, it is possible that the void will be created in space occupied by previously healthy bone or that the void may not be positioned at the location at which the injected cement will have the most effect in stabilizing the fracture.

SUMMARY OF THE INVENTION

This invention relates to a new and useful cavity creator. Specifically, this invention is related to a cavity creator that a practitioner can insert into a vertebra or other bone and from which a blade can be extended. The practitioner manipulates the cavity creator to create a cavity using the blade. Once the cavity is created, a cartridge containing bone cement or other filler material is connected to the cavity creator. Cement/bone filler is then injected through a lumen in the cavity creator into the cavity.

The cavity creator comprises an outer or access cannula, an inner or cement cannula, a blade and a knob. The blade is retracted within the cavity creator while the cavity creator is inserted in the vertebra or other tissue. When the knob is rotated, the cement cannula longitudinally translates relative to the access cannula. Translation of the cement cannula pivots the blade about a pivot pin, extending the blade radially outward of the cannulae. Once the blade is extended, the cavity creator is rotated to cause a like rotation of the blade. The rotation of the blade against the bone scrapes the bone so as to form a cavity.

The cavity creator of the instant invention does not require the practitioner to first insert the device into the patient and then insert the blade through the lumens or cannulas to create the cavity. Eliminating this step simplifies the procedure and reduces the overall amount of time it takes to perform the procedure.

BRIEF DESCRIPTION OF THE DRAWINGS

Advantages of the present invention will be readily appreciated as the same becomes better understood by reference to the following detailed description when considered in connection with the accompanying drawings in which.

DETAILED DESCRIPTION OF THE INVENTION

For the purpose of promoting an understanding of the present invention, references are made in the text hereof to exemplary embodiments of a cavity creation tool, only some of which are depicted in the figures. It should nevertheless be understood that no limitations on the scope of the invention are thereby intended. One of ordinary skill in the art will readily appreciate that modifications such as those involving the materials from which the components are made, the size of the components, functional equivalents of the elements, and the inclusion of additional elements do not depart from the spirit and scope of the present invention. Some of these possible modifications are discussed in the following description. Therefore, specific details disclosed herein are not to be interpreted as limiting, but rather as support for the claims and as a representative basis for teaching one skilled in the art to employ the present invention in virtually any appropriately detailed system, structure, or manner.

As used herein, "distal" refers towards the site to which the cavity creator is applied; "proximal" means away from the site to which the cavity creator is applied, toward the practitioner holding the cavity creator. The term "substantially" or "approximately" as used herein may be applied to modify any quantitative representation that could permissibly vary without resulting in a change in the basic function to which it is related.

Figure 1:
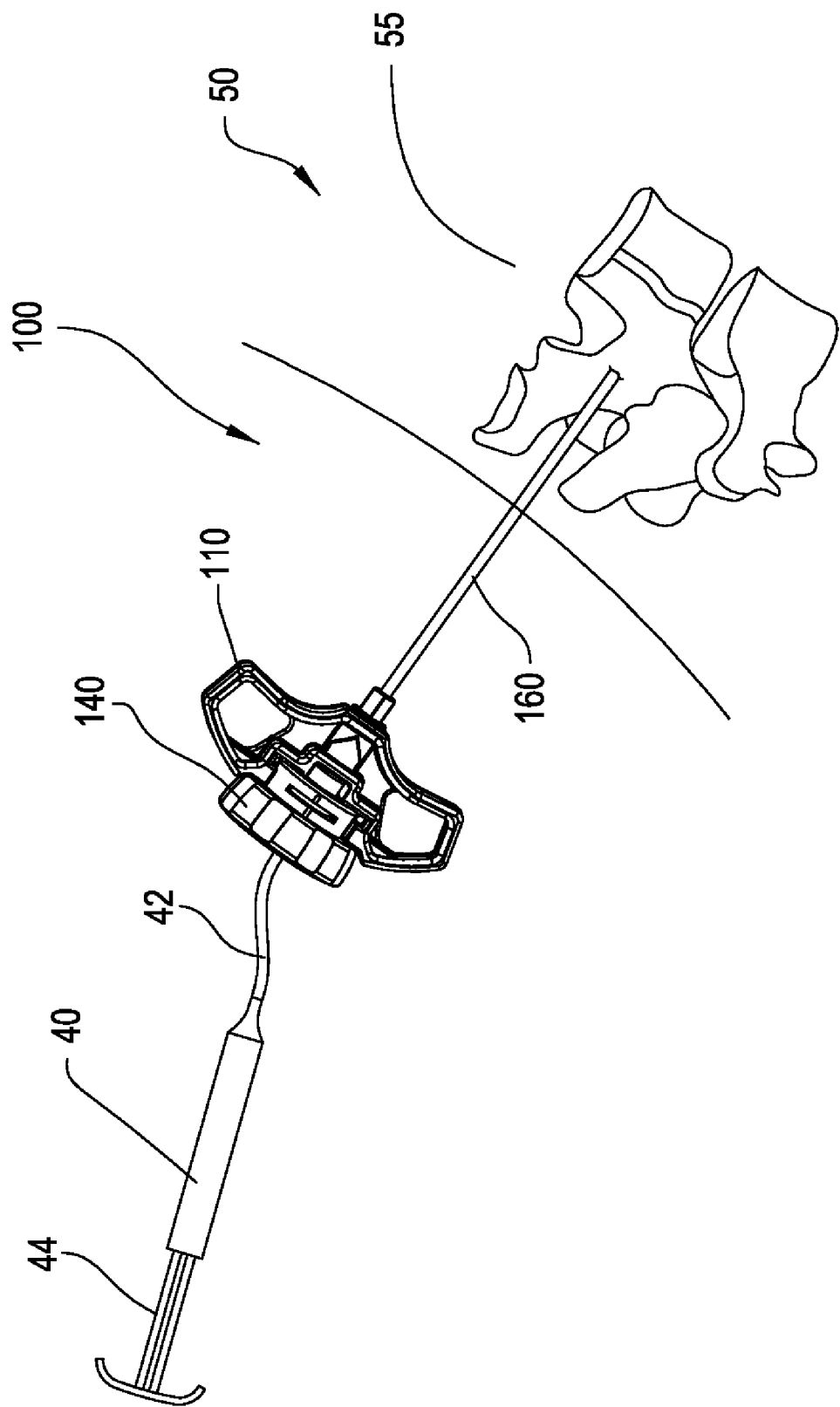
FIG. 1 is a perspective view of the cavity creator inserted into a patient's vertebra.

FIG. 1 is a perspective view of cavity creator 100 of this invention inserted into vertebra 55 of a patient 50. Cavity creator 100 comprises handle 110, knob 140, and an outer tube, access cannula 160. Distal end 164 of access cannula 160 is inserted into patient's 50 vertebra 55. Handle 110 and knob 140 are located at the proximal end of access cannula 160. Once the cavity is formed and while the cavity creator 100 remains inserted in the vertebra, cavity creator 100 is connected to cement/filler delivery cartridge 40 via flexible tube 42. Cement or other bone filler is contained within cartridge 40. When plunger 44 is depressed, the cement passes through cavity creator 100 and is injected into the cavity.

Figure 2:
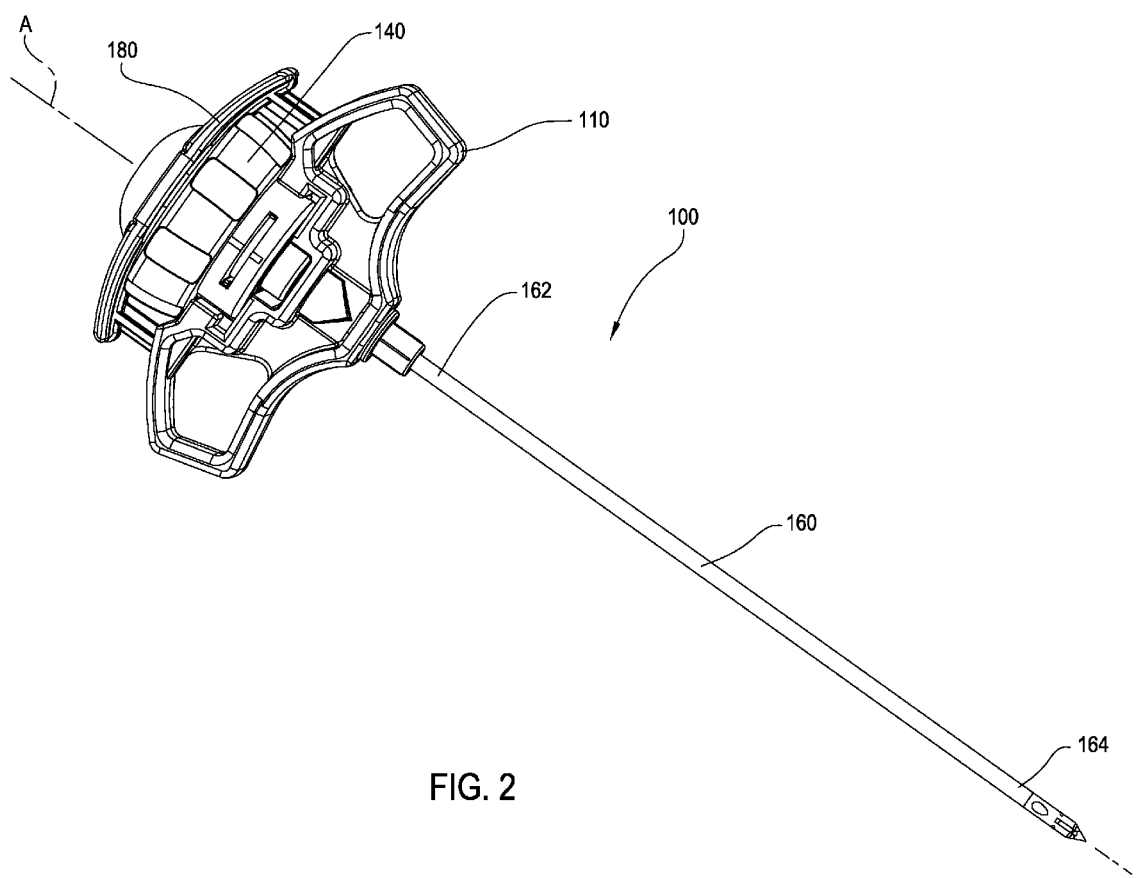
FIG. 2 is an assembly view of the cavity creator.
Figure 3:
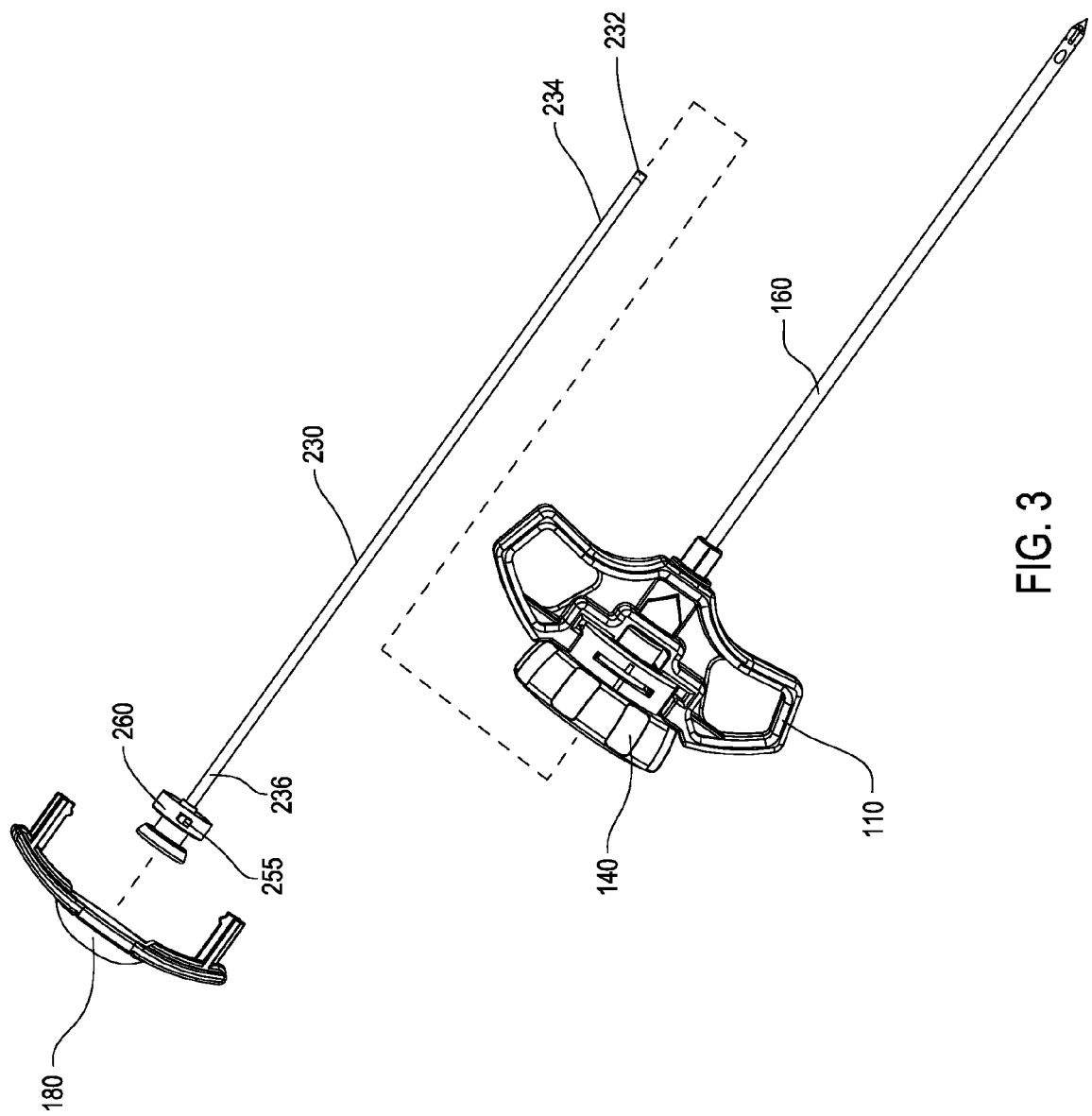
FIG. 3 is an exploded view of the cavity creator.

FIGS. 2 and 3 illustrate cavity creator 100 in which handle 110, knob 140, access cannula 160, and handle cap 180 can be seen. Access cannula 160 is a substantially hollow elongated tube and comprises proximate end 162 and an opposed distal end 164. Handle 110 is rigidly secured to proximal end 162 of access cannula 160. Tip 170 is attached to the distal end of an inner tube, cement cannula 200 (see FIG. 13). Tip 170 extends forward from distal end 164 of access cannula 160. Tip 170 functions as the component that punctures the patient's skin and vertebra or other bone into which cavity creator 100 is inserted. The cement cannula 200 has a lumen 202 that extends axially therethrough (see FIG. 13). The cement cannula 200 is positioned substantially within the access cannula 160. Blade 210 is pivotally connected to access cannula 160 and seated within cement cannula 200.

Stylet 230 is a substantially solid elongated rod that is removably positioned within cement cannula 200. Handle cap 180 keeps stylet 230 within cavity creator 100 until the practitioner intends to remove stylet 230 from cavity creator 100.

When knob 140 is rotated about Axis A, cement cannula 200 functions as a drive member by being longitudinally displaced relative to access cannula 160. This displacement of the cement cannula 200 pushes the pivoting blade 210 against the access cannula. This displacement of blade 210 causes the blade to rotate about pivot pin 220 to extend blade 210 radially outward from cavity creator 100 or access cannula 160. Cavity creator 100 is then rotated and/or raised and lowered so that blade 210 can scrape the bone to create the cavity. In the embodiment shown, knob 140 is made of Nylon 6 6 plastic as manufactured by EMS-Grivory of Sumter, South Carolina, but can be made of any material commonly known and used in the art having similar characteristics.

Also visible in FIGS. 2 and 3 is handle cap 180. Handle cap 180 extends over knob 140 and is removably secured to handle 110 to prevent removal of stylet 230 and rotation of knob 140. Handle cap 180 also allows the practitioner to use a hammer or other device to aid in inserting cavity creator 100 into the vertebra without damaging the other components of cavity creator 100. Handle cap 180 is made of the same material as knob 140, but can also be made of another material and need not be made of the same material as knob 140.

Figure 4:
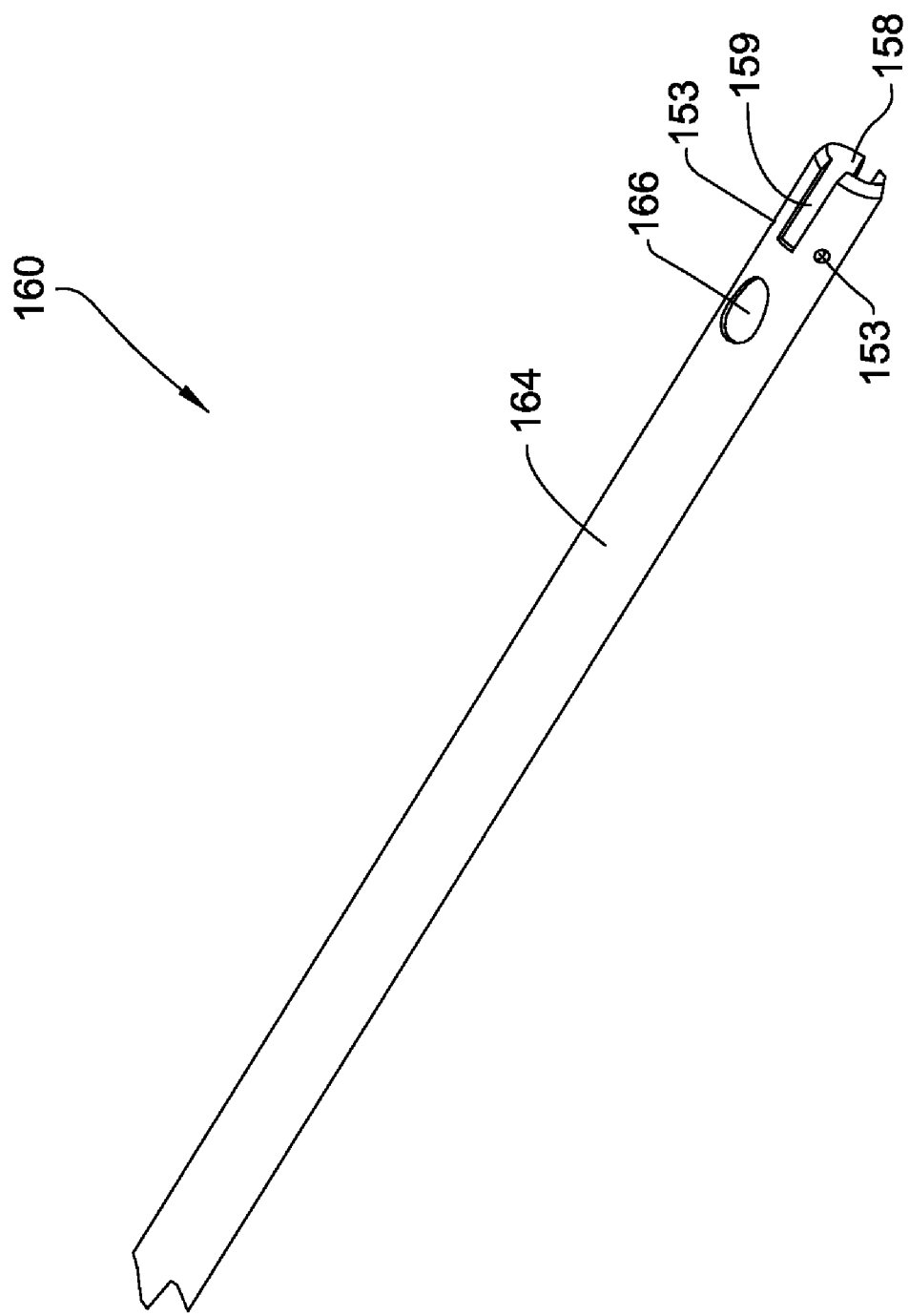
FIG. 4 is a perspective view of the distal end of the access cannula.

FIG. 4 illustrates distal end 164 of access cannula 160. Center bore 158 extends end-to-end through access cannula 160. A pair of diametrically opposed, rectangularly shaped slots 159 extend proximally rearward from distal end 164 of access cannula 160. Each slot 159 is contiguous with access cannula bore 158. A pair of holes 153 is formed in access cannula 160 between the slots. Holes 153 are located immediately forward of proximal end 164 of slot 159. Holes 153 are centered on a line located above the longitudinal axis of access cannula bore 158. The line along which the holes 153 are centered is closer to one of the two slots 159 than the other of the two slots 159. Proximally rearward of slots 159, access cannula 160 is formed to define discharge port 166. More particularly, access cannula 160 is formed so that discharge port 166 is longitudinally aligned with one (1) of slots 159. Access cannula 160 is shaped so that discharge port 166 has an elliptical shape.

Figure 5:
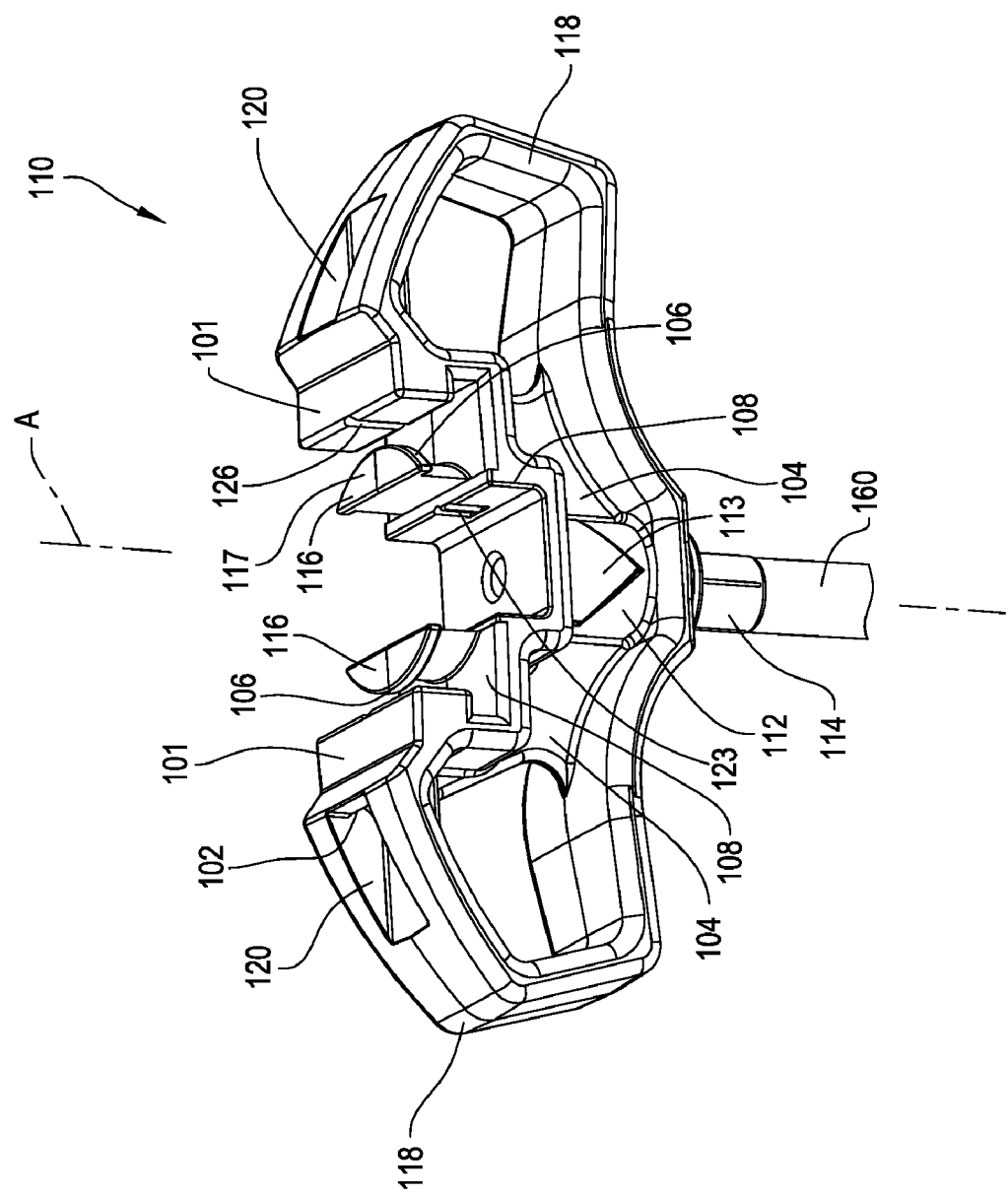
FIG. 5 is a top perspective view of the handle of the cavity creator.
Figure 6:
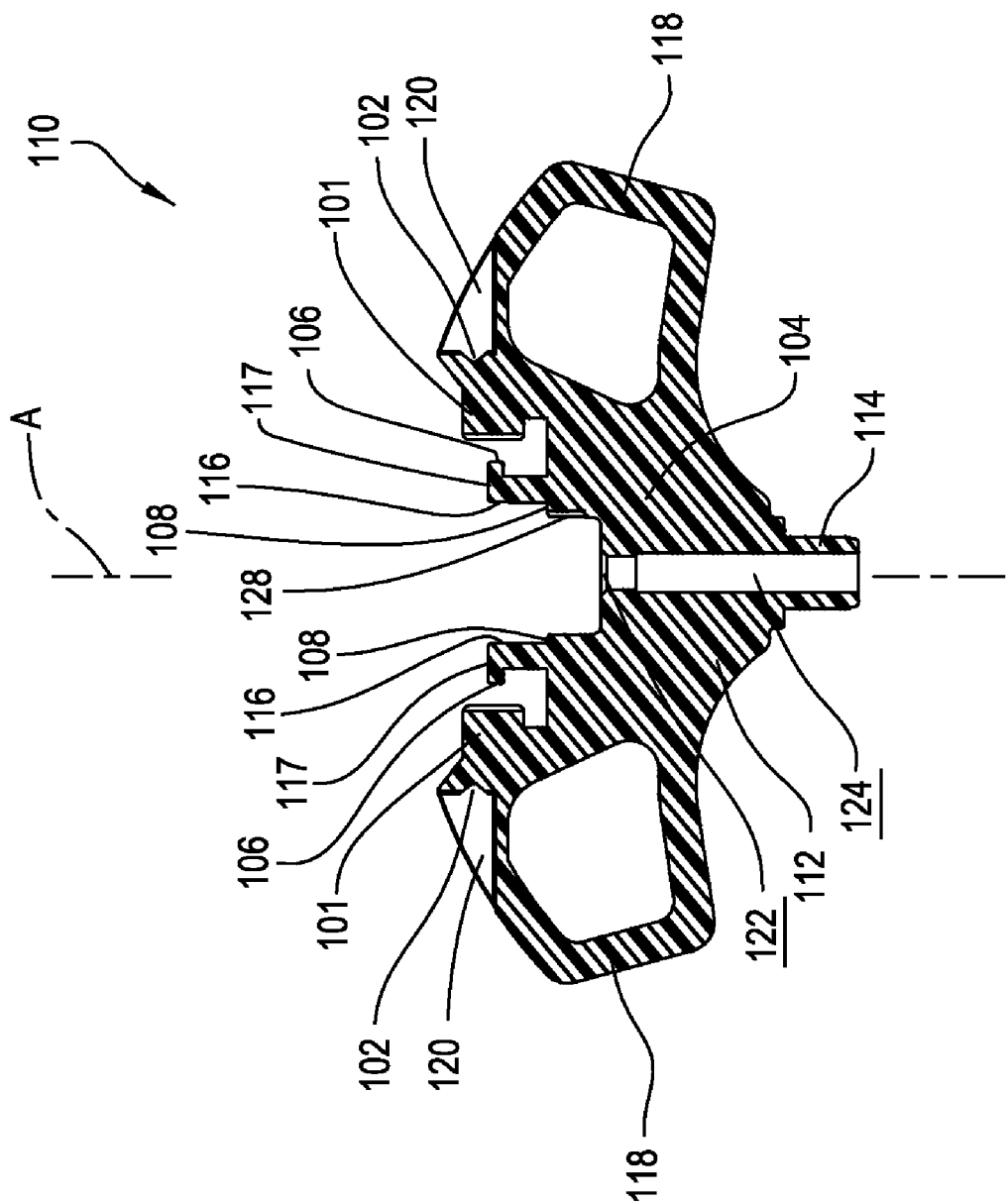
FIG. 6 is a cross-sectional view of the handle shown in FIG. 5.

FIGS. 5 and 6 illustrate handle 110. Handle 110 has a cylindrical neck 114 that forms the distal end of handle 110. Above neck 114, handle 110 is formed to have cylindrical core 112. Core 112 has an outer diameter greater than that of neck 114. A single arcuately shaped shoulder 113 extends outwardly from an outer surface of core 112. Shoulder 113 has a distal end (not identified) that is V-shaped and directed towards the distal end of cavity creator 100. More particularly, shoulder 113 is located on handle 110 so that the distally base of the shoulder points to access cannula slot 159 from which blade 210 emerges. The proximal end of core 112 has a flat shape.

Two opposed steps 108 formed integrally with core 112 extend upwardly from the opposed sides of the proximal end of core 112. Steps 108 have a length greater than that of the diameter of core 112 such that each step 108 extends outwardly from core 112. One (1) tab 116 extends upwardly from each step 108. Each tab 116 generally has a cross-sectional shape of slice section through the end of a circle. Tabs 116 are located so that each tab 116 is slightly set back from the horizontal surface-vertical surface edge of step 108 with which tab 116 is integral. Each tab 116 is further formed to have around top surface 117 a lip 106 that projects outwardly around the curved outer surface of tab 116.

Opposed arms 118 project outwardly from handle core 112. Each arm 118 is in the form of a three-section structure (individual sections not identified). A first section of each arm 118 projects outwardly from the distal end of core 112, adjacent handle neck 114. A second section of an individual arm 118 extends upwardly from the outer end of the first section. Each arm 118 has a third section that extends inwardly from the top of the second section. The third section of each arm 118 curves downwardly and connects to the adjacent step 108. The first and second sections of each arm 118 are generally planar structures. The third section of each arm 118 is formed to so that as arm 118 approaches adjacent step 108, the thickness of arm 118 increases.

A downwardly extending recess 120 is formed in the top surface of the third section of each arm 118. Generally, handle 110 is shaped so that each recess 120 is defined by abutting horizontal and vertical surfaces on arms 118 (surfaces not identified). Handle 110 is further formed to define groove 102 in each recess-defining vertical surface of arm 118. Each groove 102 extends the width of the vertical surface and is located a short distance above the horizontal surface that defines the base of recess 120.

Finger 101 extends inwardly from the third section of each arm 118. Each finger 101 extends from the surface of the associated arm 118 that curves downwardly towards the end of the adjacent step 108. Fingers 101 project over and above the horizontal surfaces of the adjacent steps 108. Each finger 101 is generally in the form of an elongated bar that extends the width of arm 118 from which each finger 101 extends. A small groove 126 is formed in the inner face of each finger that is directed to the opposed finger 101. Each groove 126 extends the top to bottom length of finger 101 with which groove 126 is integral. Grooves 126 are located along the top-to-bottom longitudinal axes of fingers 101.

Figure 7:
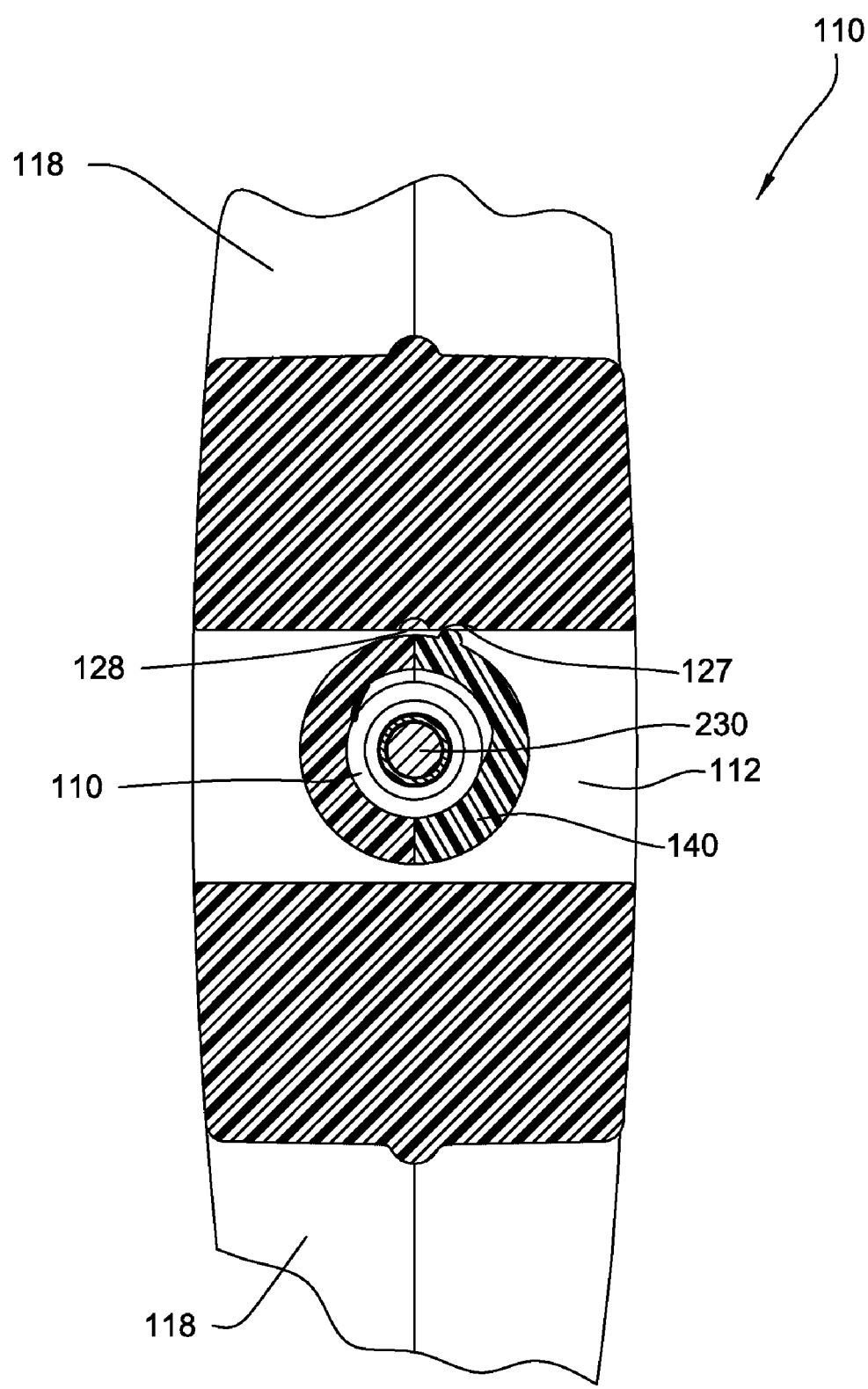
FIG. 7 is cross-sectional view of the cavity creator through the handle along a plane perpendicular to the longitudinal axis of the cavity creator.

Two grooves 127 and 128, best seen in FIG. 7, are formed on the vertical surface of a single one (1) of steps 108. Both grooves 127, 128 are aligned on axes parallel to the longitudinal axis of cavity creator 100. A first of the grooves, groove 127, has a relatively shallow depth. The second groove, groove 128, is of deeper depth than groove 127. Both grooves 127 and 128 have a generally circular cross sectional profile. Groove 128 has a smaller radius of curvature than groove 127.

Figure 16:
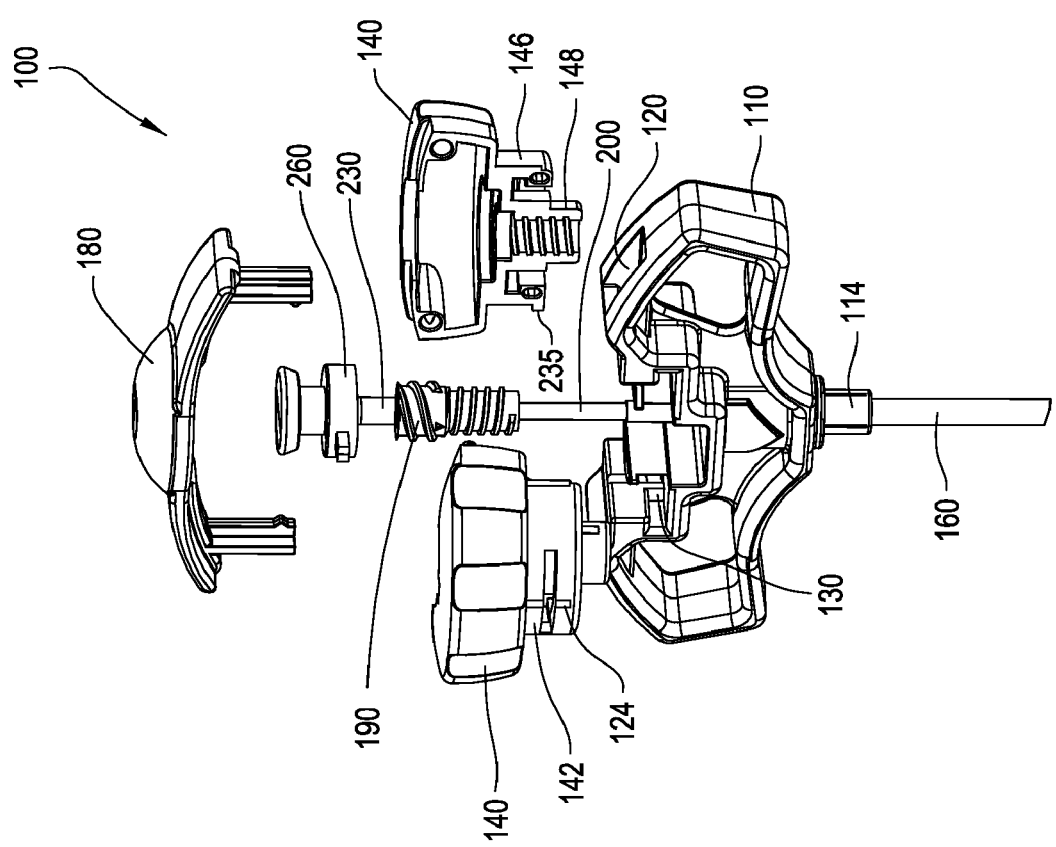
FIG. 16 is an exploded view of the proximal end of the cavity creator.

Handle 110 is further formed with a stop 130 (FIG. 16). Stop 130 is in the form of a rectangular and planar shaped web that extends downward from one finger 101 to the horizontal surface of the step 108 below the finger. More particularly, stop 130 is located above the step 108 opposite the step 108 in which grooves 127 and 128 are formed. Stop 130 should also be understood to project outwardly from the vertical wall (not identified) that extends between the associated finger 101 and step 108.

Handle 110 is further formed to have a pair of opposed webs 104. Webs 104 extend outwardly from opposed surfaces of handle core 112. Each web 104 extends bottom-to-top from the opposed surfaces of handle arm 118 first and third surfaces between which web 104 is located. Webs 104 thus provide structural strength to handle 110.

First and second contiguous and coaxial bores 122 and 124, extend through handle core 112 and neck 114. Bore 122 extends downwardly from the top surface of handle core 112. (Not identified is the small tapered counter bore that forms the actually opening in core 112 top surface.) Bore 122 has a diameter that allows cement cannula 200 to slidably move within the bore 122. The distal end of bore 122 opens into bore 124. Bore 124 extends from bore 122 to the distal end of handle neck 114. Bore 124 has a diameter greater than that of bore 122. More particularly, bore 124 has a diameter that allows access cannula 160 to be seated and secured in bore 124. In some versions of the invention, access cannula 160 is heat staked, overmolded, or adhesively secured in bore 124.

It should be understood that handle steps 108 are not equidistantly spaced apart from bore 122. The step 108 in which grooves 127 and 128 are formed is closer to bore 122 than the opposed step 108. Consequently, the step 108 in which the grooves 127 and 128 is longer in width, the lateral axis across the handle 110, than the opposed step 108.

Figure 8:
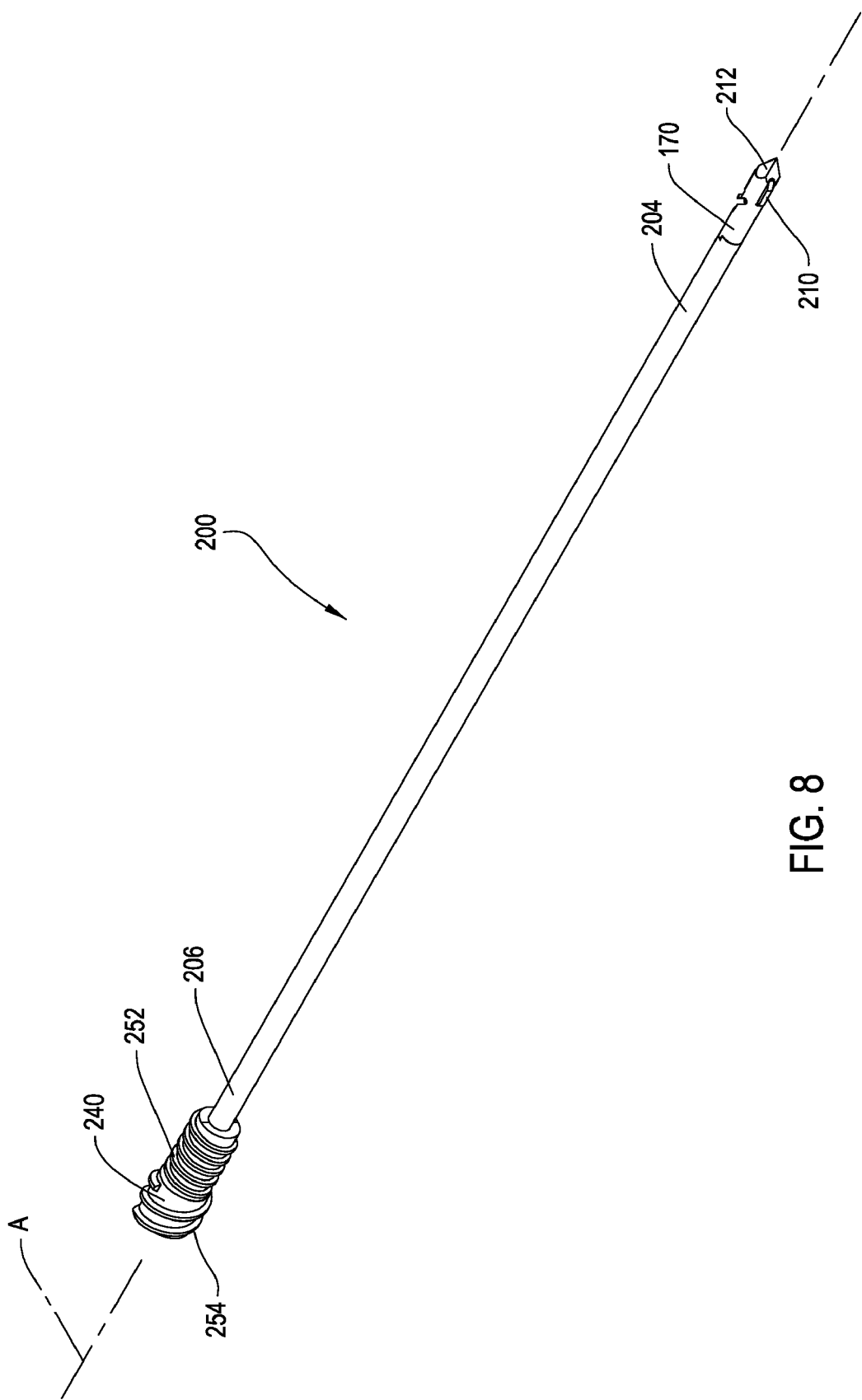
FIG. 8 is a perspective view of the cement cannula with the luer hub attached.
Figure 13:
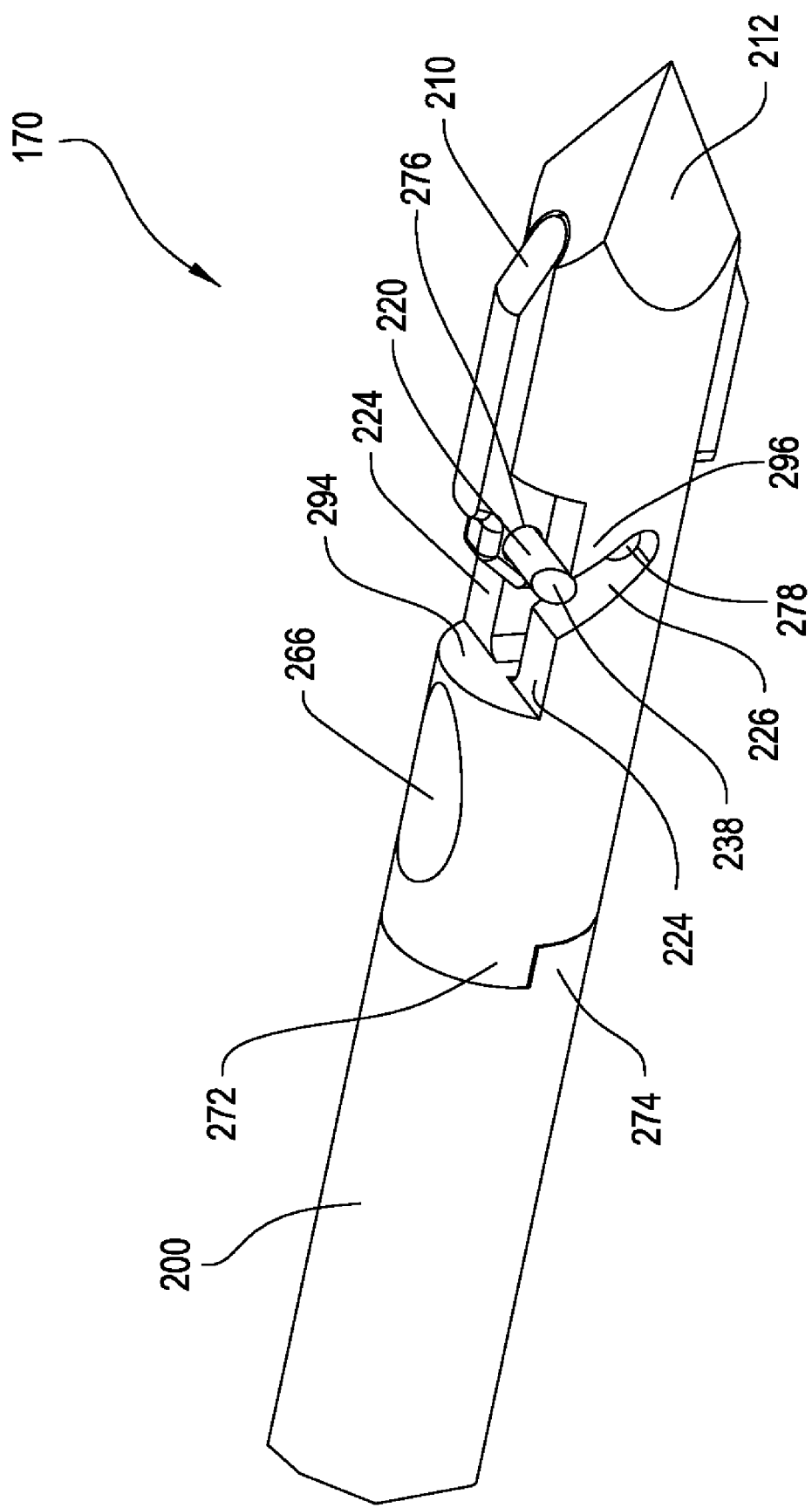
FIG. 13 is a perspective assembly view of the pivot pin and blade positioned within the cement cannula.

FIG. 8 is a perspective view of cement cannula 200. Cement cannula 200 is also a substantially hollow elongated shaft and comprises distal end 204. Cement cannula 200 has an outer diameter that allows the cement cannula to slidably move within bore 158 of access cannula 160. Lumen 202 extends axially through cement cannula 200. Cement cannula 200 is further formed to have at distal end 204 a forwardly extending lip 274 (FIG. 13). Lip 274 is generally arcuately shaped.

Cement cannula 200 is made of 304 non-hardened stainless steel. Tip 170 is made of 17-4 pre-hard, heat treatable stainless steel. However, one of ordinary skill in the art will recognize that cement cannula 200 and tip 170 can be made of any sufficiently corrosion resistant, biocompatible, rigid material and that cement cannula 200 and tip 170 can also be made of the same material.

Figure 9:
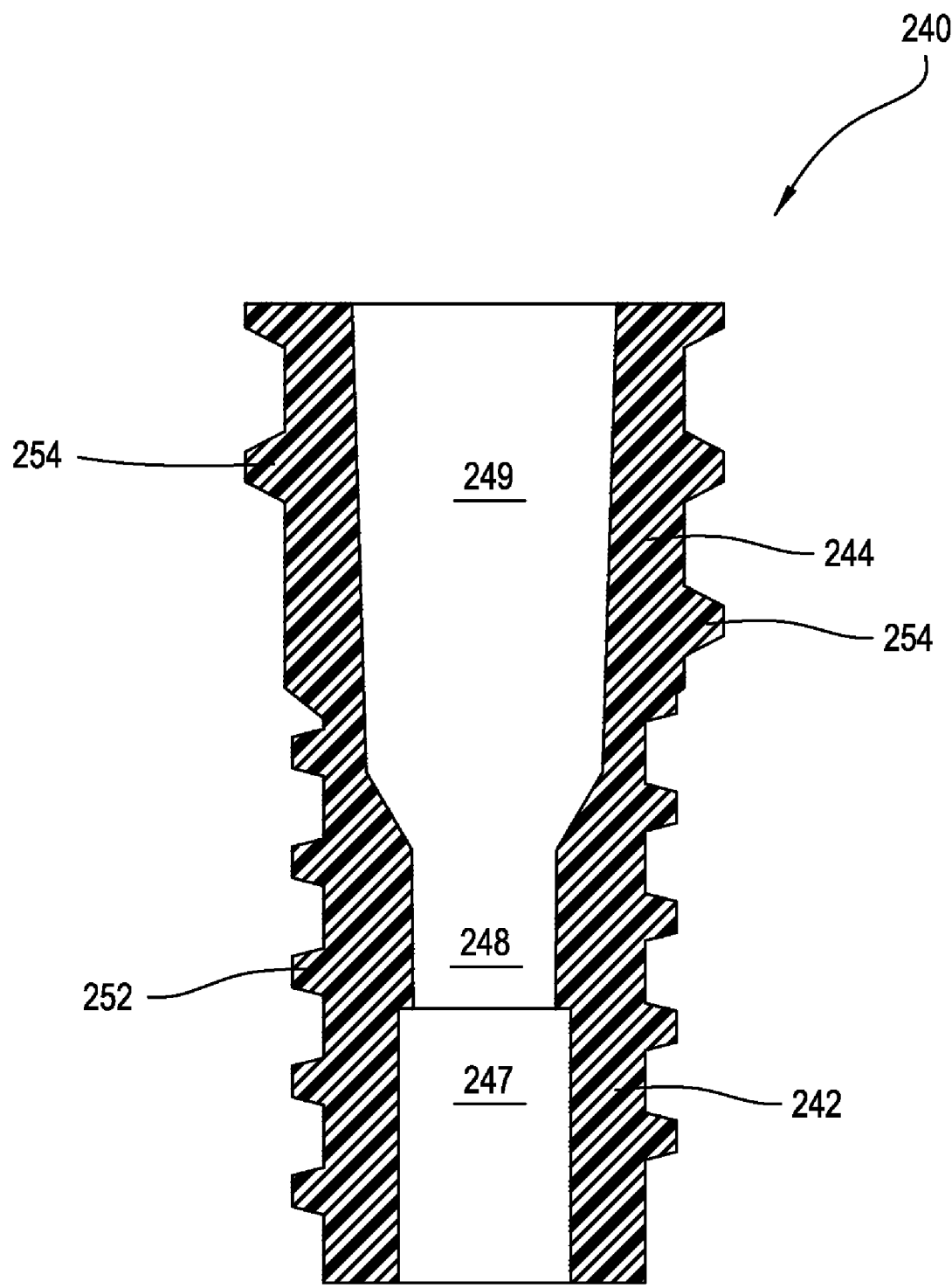
FIG. 9 is a cross-sectional view of the luer hub shown in FIG. 8.

Luer hub 240 is secured to proximal end 206 of cement cannula 200. As best seen in FIG. 9, luer hub 240 is formed from a single piece of plastic that is shaped to have base 242 and head 244 coaxial with base 242. Both base 242 and head 244 are generally cylindrical. Head 244 is located above base 242 and has an outer diameter slightly greater than that of base 242. A first bore 247 extends upwardly from the distal end of base 242. Bore 247 is dimensioned to receive the proximal end of cement cannula 200. Bore 247 extends approximately one quarter the way up luer hub 240 from the bottom of hub base 242. A second bore, bore 248, extends upwardly through hub base 242 from bore 247 towards the top end of hub base 242. Bore 248 has a diameter less than that of bore 247. More particularly, bore 248 has a diameter that allows stylet 230 to be slidably advanced/retracted through bore 248. Luer hub 240 has a third bore, bore 249, that extends upwardly from second bore 248. Bore 249 has a diameter greater than the diameter of stylet 230. Third bore 249 is located in and extends axially through hub head 244. Bore 249 has a diameter that is greater than the diameter of bore 248. (Not identified is the sloped surface between second bore 248 and third bore 249.) In some versions of the invention, bore 249 also has a diameter greater than that of bore 247. While not readily visible in the Figures, third bore 249 is also tapered inward along its length from its proximal end to its distal end. The taper allows luer hub 240 to connect to a luer fitting of a standard syringe or other medical device. For example, while the distal end of tube 42 is not shown, this tube would have a fitting that allows the tube to be connected to luer hub 240.

Threading 252 is disposed about the outer surface of hub base 242. As discussed below, threading 252 engages complementary threading integral with knob 140 to extend and retract cement cannula 200. Luer hub 240 is also formed with threading 254 around hub head 244. Threading 254 is dimensioned to engage complementary threading associated with a luer fitting used to attach flexible delivery tube 42 to cement cannula 200.

Figure 10:
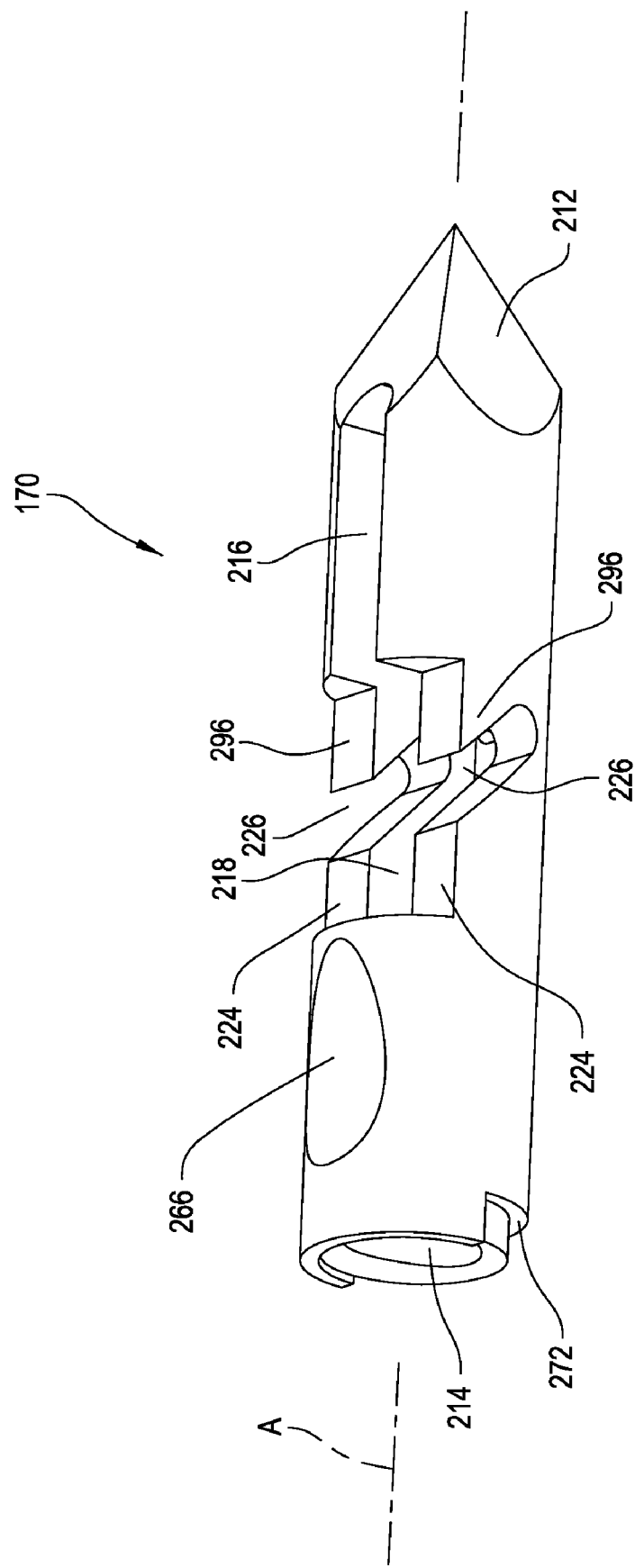
FIG. 10 is a longitudinal perspective view of the distal end of the cement cannula shown in FIG. 8.

FIG. 10 illustrates tip 170, which is attached to distal end 204 of cement cannula 200. Tip 170 is generally cylindrically shaped. Tip 170 is formed to have a solid, diamond shaped head 212. The geometry of head 212 allows head 212 to puncture the soft and hard tissue into which cavity creator 100 of this invention is inserted. Tip 170 is shaped to form bore 214 (see FIG. 14) that extends forward from the proximal end of tip 170. Bore 214 angles upward into cement discharge port 266 formed along an outer circumferential surface of tip 170. In the illustrated version of the invention, an arcuate step 272 is formed in tip 170 around the proximal end of tip 170. Step 272 does not extend circumferentially around tip 170 and is not contiguous with the opening of bore 214. As seen in FIG. 13, when cavity creator 100 of the instant invention is assembled, cement cannula lip 274 seats in the void space defined by step 272. This lip-in-slot arrangement ensures that during manufacture, tip 170 assumes the proper orientation relative to cement cannula 200. This lip-in-slot arrangement also facilitates the torsional strength of the tip-to-cement cannula coupling.

Referring again to FIG. 10, tip 170 is also formed to have blade slot 216 that is located proximal to tip head 212 and forward of discharge port 266. Blade slot 216 extends through tip 170 from the top to the bottom. Supplemental slot 218, which is contiguous with blade slot 216, extends rearwardly in tip 170 from blade slot 216. It should further be understood that tip 170 is formed so that the longitudinal axis of discharge port 266 lies in the longitudinal plane around which slots 216 and 218 are centered. Discharge port 266 is centered along a plane that is perpendicular to the longitudinal plane around which slots 216 and 218 are centered. Unlike blade slot 216, supplemental slot 218 does not extend completely through the opposed top and bottom sides of tip 170.

Tip 170 is also formed to define parallel notches 224 on either side of the open end of supplemental slot 218. The bases of notches 224 lie along a plane that is perpendicular to the longitudinal plane around which slots 216 and 218 are centered. The proximal ends of each notch 224 start along a plane located forward of discharge port 266. Notches 224 extend forward along tip 170 to intersect the proximal end of blade slot 216.

Parallel slots 226 extend downwardly from the base of each notch 224. Slots 226, which start at a position approximately in the middle of each notch 224, extend forward at approximately a forty five degree (45°) angle towards blade slot 216. As shown, each slot 226 traverses the entire thickness of each opposing side of tip 170.

Figure 11:
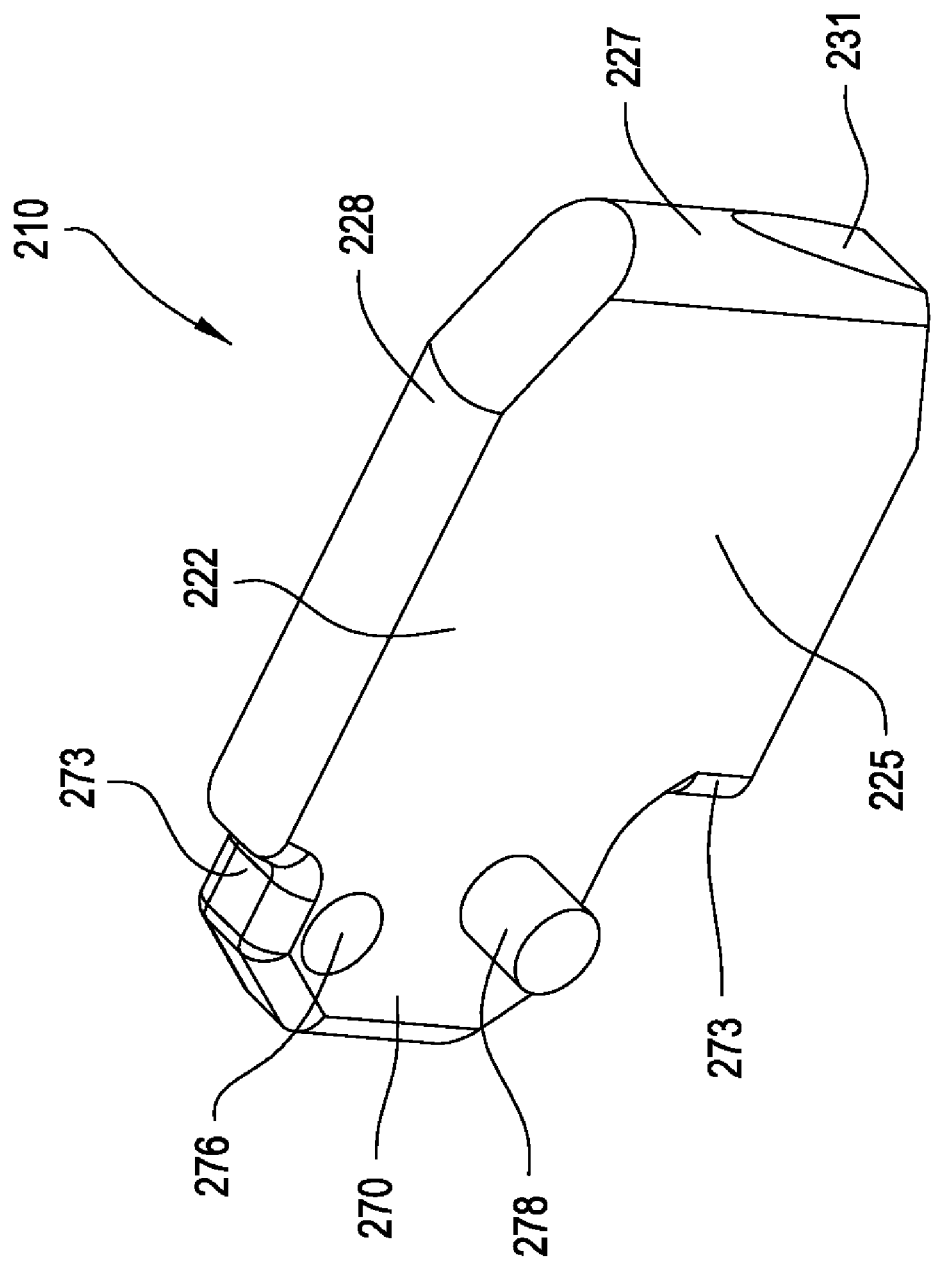
FIG. 11 is a perspective view of one embodiment of the blade.

FIG. 11 is a perspective view of blade 210. Blade 210 is formed from material such as 17-4 pre-hard, heat treatable stainless steel, but can also be made of any commonly known and used material in the art having similar characteristics. Blade 210 comprises body 222 that has a generally planar shape. Body 222 has main section 225 that has a top-to-bottom height substantially equal to the outer diameter of access cannula 160. Inherently, this dimension is greater than the top-to-bottom height of tip blade slot 216. Body main section 222 has a leading edge 228 that has a curved cross-sectional profile. Body main section 222 has trailing edge 229 (see FIG. 14). The leading and trailing edges, 228 and 229 respectively, of blade 210 have a common radius of curvature substantially equal to the radius of curvature of access cannula 160.

Blade body 225 has distal face 227 is the most distally directed surface of the blade body 225. Distal face 227 extends between the opposed sides of the blade body 225. Face 227 generally has a rounded shape. Face 227 is further formed to have a planar taper 231 that extends forward from the distal end of trailing edge 229. Taper 231 provides clearance for blade 210 so the blade can rotate in and out of tip blade slot 216.

Blade body 225 is further formed to have a tail 270 that extends rearward and is coplanar with main section 225. Tail 270 has a top to bottom height less than that of body main section 225. More particularly, blade 210 is shaped so that when blade main section 225 seats in blade slot 216, blade tail 270 seats in supplemental slot 218 and tail 270 extends into the void space subtended by tip notches 224. The upper edge of blade tail 270 is located below leading edge 228 of main section 225. Blade tail 270 further comprises tapered corners 273 located forward of the proximal end of blade tail 270.

Throughhole 276 extends side-to-side through blade tail 270 immediately below the top edge of tail 270. Opposed posts 278 extend outwardly from the opposed sides of blade tail 270. Posts 278, which are cylindrical, are located forward and below throughhole 276. Posts 278 fit within slots 226.

Figure 12:
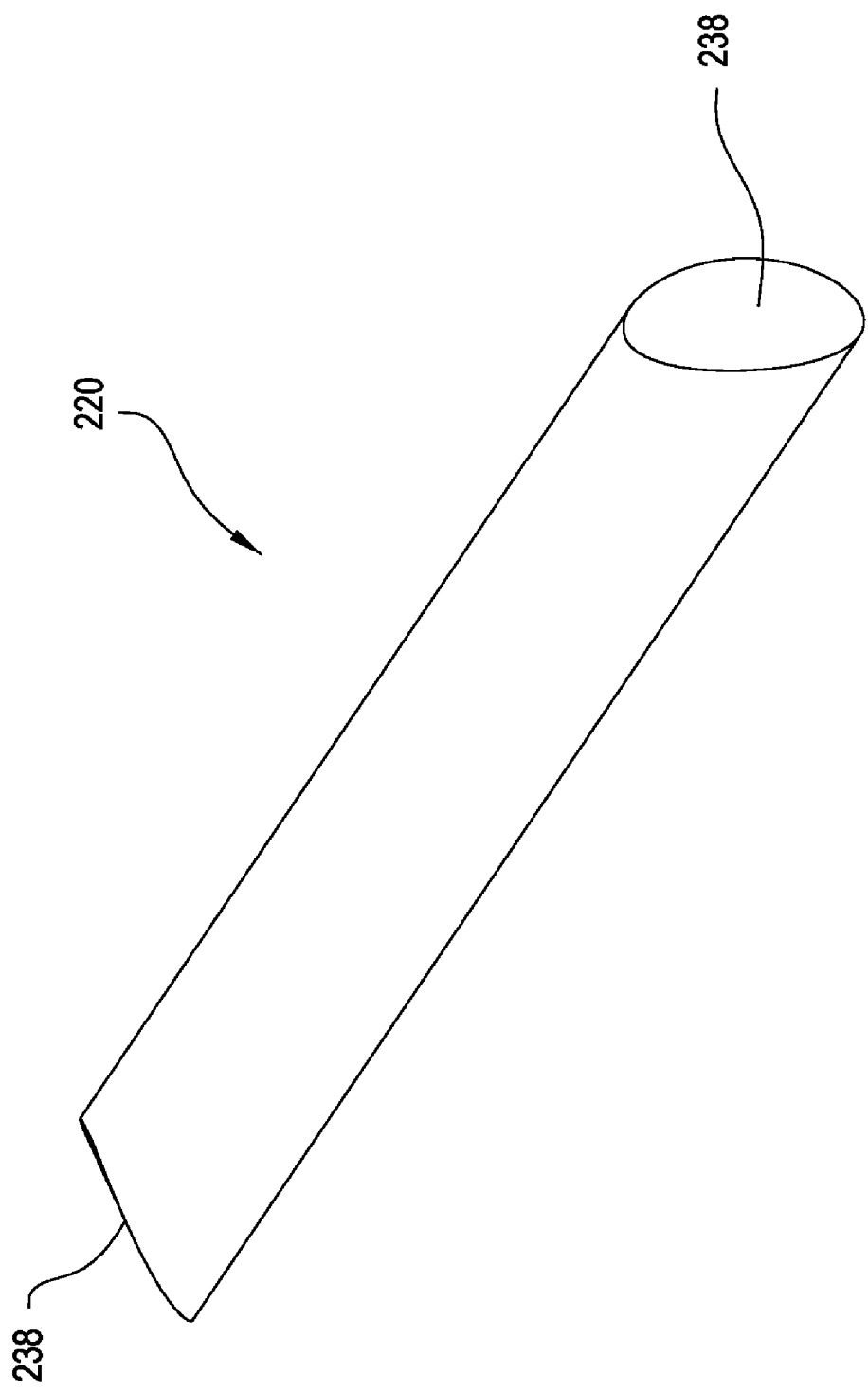
FIG. 12 is a perspective view of one embodiment of the pivot pin.

FIG. 12 is a perspective view of pivot pin 220. Pivot pin 220 is substantially cylindrical and comprises two (2) opposing outer surfaces 238. Outer surfaces 238 are slightly arcuate to correspond to the rounded outer surface of access cannula 160. While not apparent in the drawings, pivot pin 220 is slightly tapered along its length, with the diameter of the of one end being slightly larger than the diameter of the opposed end.

Figure 14:
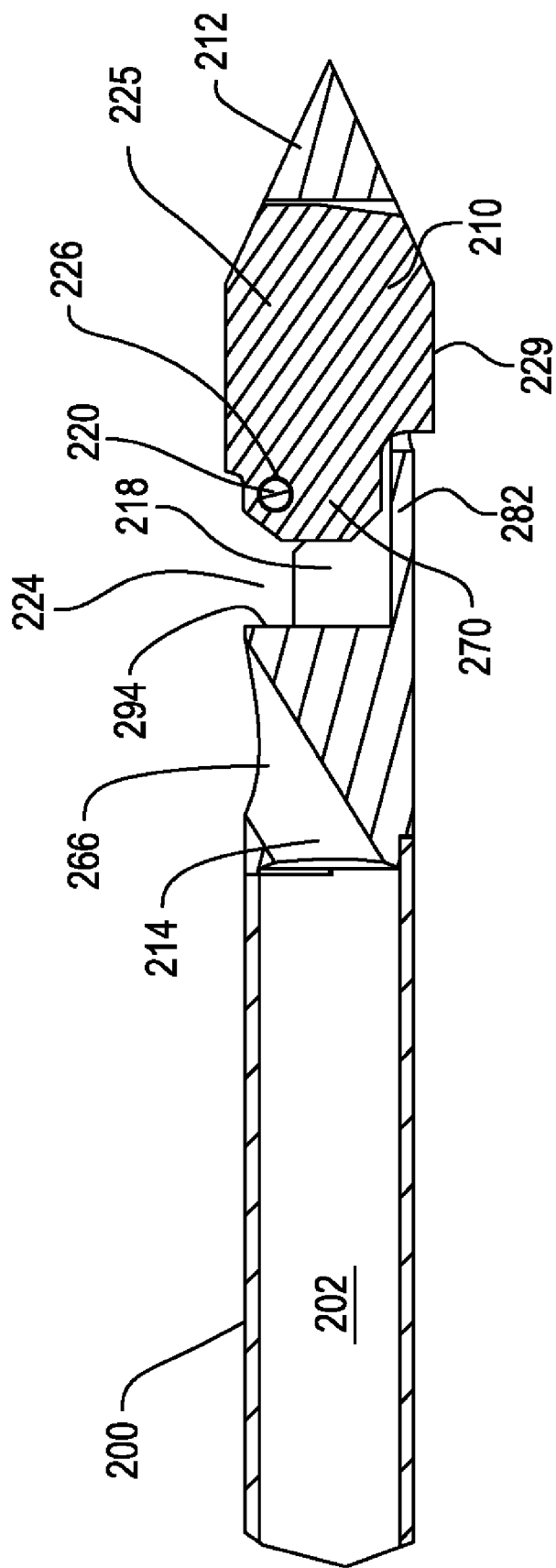
FIG. 14 is a cross-sectional view of the cement cannula, blade, and pivot pin shown in FIG. 13.
Figure 15:
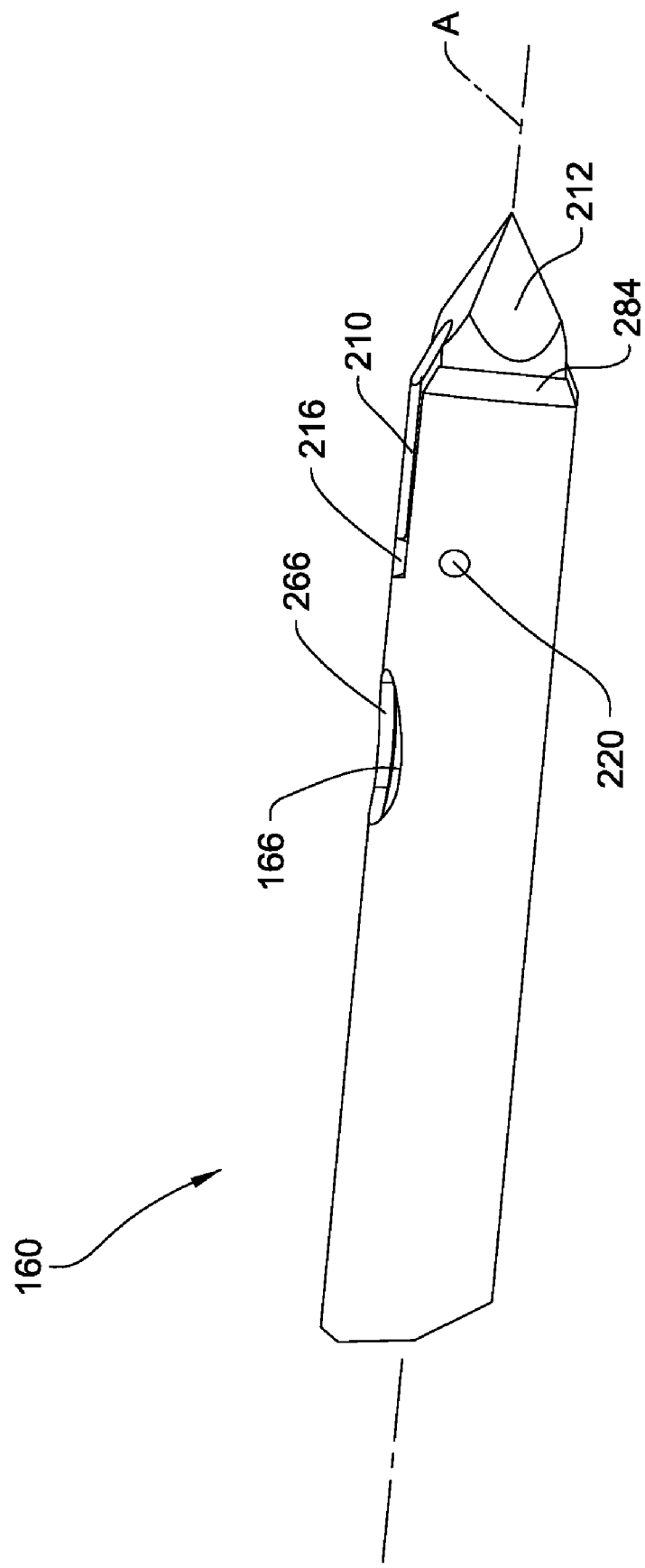
FIG. 15 is a side perspective view of the distal end of the cavity creator showing the blade seated within the tip and access cannula.

As seen by reference to FIGS. 13, 14 and 15, when cavity creator 100 is assembled, pivot pin 220 extends through blade throughhole 276. Blade 210 is positioned in tip 170 so that body main section 225 of blade 210 seats in tip blade slot 216 and body tail 270 seats in supplemental slot 218. Owing to the relative dimensions of tip 170 and blade 210, the opposed side edges of blade 210 project beyond the outer circumferential surface of tip 270. As a consequence of the seating of blade 210 in tip 170, each post 278 seats in an adjacent tip slot 226. The opposed ends of pivot pin 220 extend through and over and beyond notches 224. Owing to the shaping of access cannula 160 and pivot pin 220, the arcuately shaped opposed outer surfaces 238 of pivot pin 220 are flush with the outer circumferential surface of access cannula 160.

Upon assembly of cavity creator 100, distal end 164 of cement cannula 200 and the portion of tip 170 proximal to head 212 are seated within access cannula bore 158. Tip blade slot 216 is in registration with the opposed access cannula slots 159. The opposed ends of pivot pin 220 are fixedly secured via press fit in the opposed access cannula holes 153. One access cannula hole 153 is slightly larger than the other such that each end of pivot pin 220 can be press fit within each access cannula hole 153. Specifically, upon assembly, the end of pivot pin 220 having a smaller diameter is slid through access cannula hole 153 having a larger diameter and into access cannula hole 153 having a smaller diameter. The result is that pivot pin 220 can be slid along the width of access cannula 160, but each end press fit within the corresponding access cannula hole 153.

Lumen 202 leads into tip bore 214 at approximately a 30° angle relative to Axis A to form discharge port 266.

Tip 170 further includes projection 282, which is below tail 270 of blade 210 and extends forward to form the bottom surface of tip 170. Projection 282 is therefore arcuately shaped. Projection 282 also forms the bottom of supplemental slot 218, but does not extend to head 212. Because it does not extend along the entire length of tip 170, projection 282 allows blade slot 216 to traverse tip 170 from top to bottom.

Owing to the relative dimensioning of access cannula 160 and blade 210, when in the retracted position (for example, as shown in FIG. 15), blade 210 is substantially flush with access cannula 160 so as not to catch on tissue when cavity creator 100 is inserted into the patient. Also visible in FIG. 15 is tapered surface 284 around the distal end of tip 170. Tapered surface 284 is angled inward between the diameter of access cannula 160 and approximately the outer diameter of head 212. Tapered surface 284 further reduces the likelihood of access cannula 160 catching tissue when cavity creator 100 is inserted in the patient.

It should be appreciated that a feature of this invention is that blade 210 extends forward from tip 170 as close as possible to the distal end and that cement discharge port 266 is open as close as possible to the distal end of the tip 170. To facilitate these design criteria, blade is formed with taper 231. Taper 231 has a slope that makes it possible to minimize the distance between the distal end of blade 210 and the adjacent inner wall of tip 170 that defines the distal end of blade slot 216. Similarly, the proximally directed corners 269 of blade tail 270 are tapered (tapers not identified). These tapers reduce the spacing between the blade tail 270 and the distally directed internal surface of the tip that defines the proximal end of slot 216. These features make it possible to construct the tip so that in many versions of the invention, the maximum distance the distal end of the tip head 214 and the proximal ends of slots 224 is no greater than 0.200 inches. In more preferred versions of the invention, this maximum separation between these two features of tip 170 is no more than 0.150 inches. In turn, this makes it possible to fabricate tip 170 so that the cement discharge port 266 opens within 0.250 inches of the distal end of the tip and, in more preferred versions of the invention, within 0.200 inches of this end. Ideally bore 214 should be relatively wide to facilitate the discharge of cement with as free as flow as possible. In some versions of the invention bore 214 should have a diameter of at least 0.050 inches.

Figure 17:
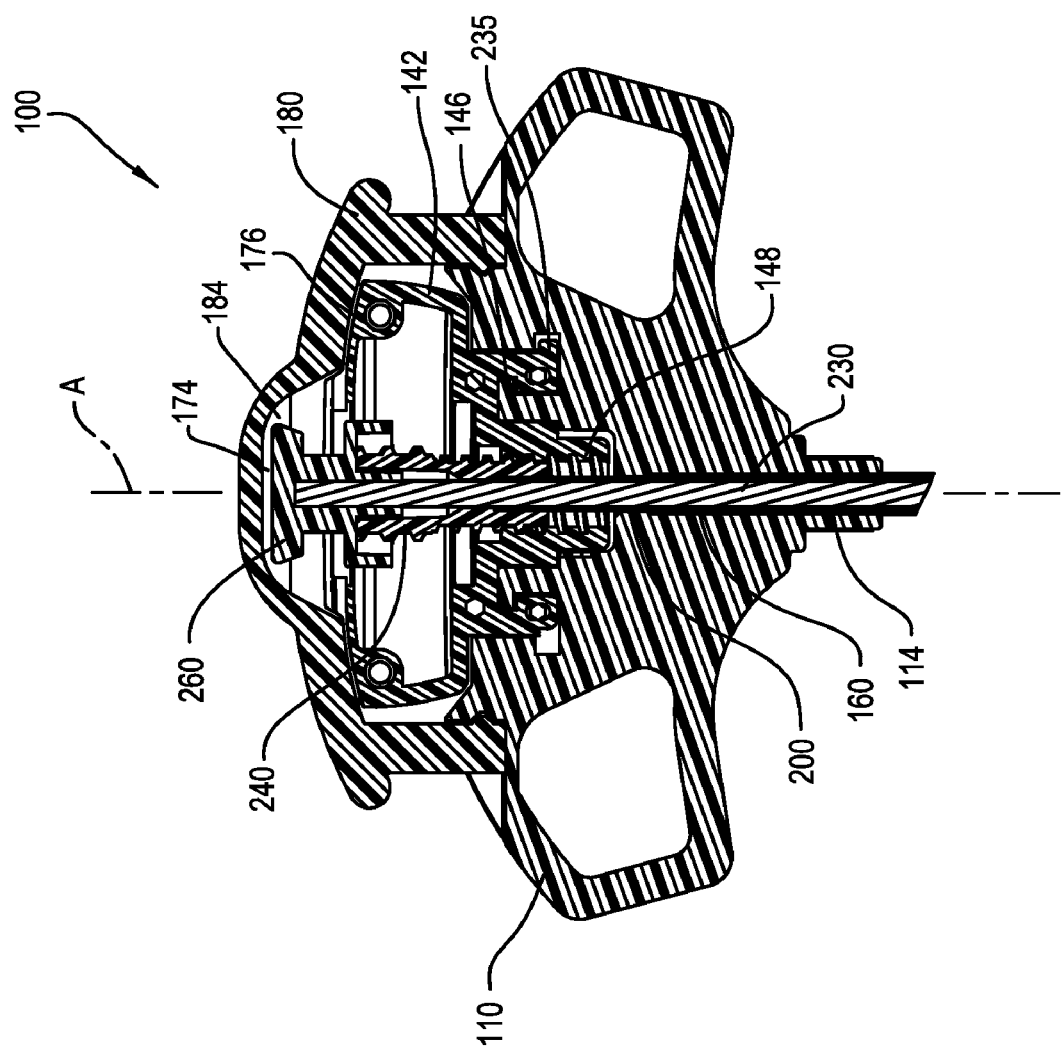
FIG. 17 is a cross-sectional view of the proximal end of the cavity creator.
Figure 18:
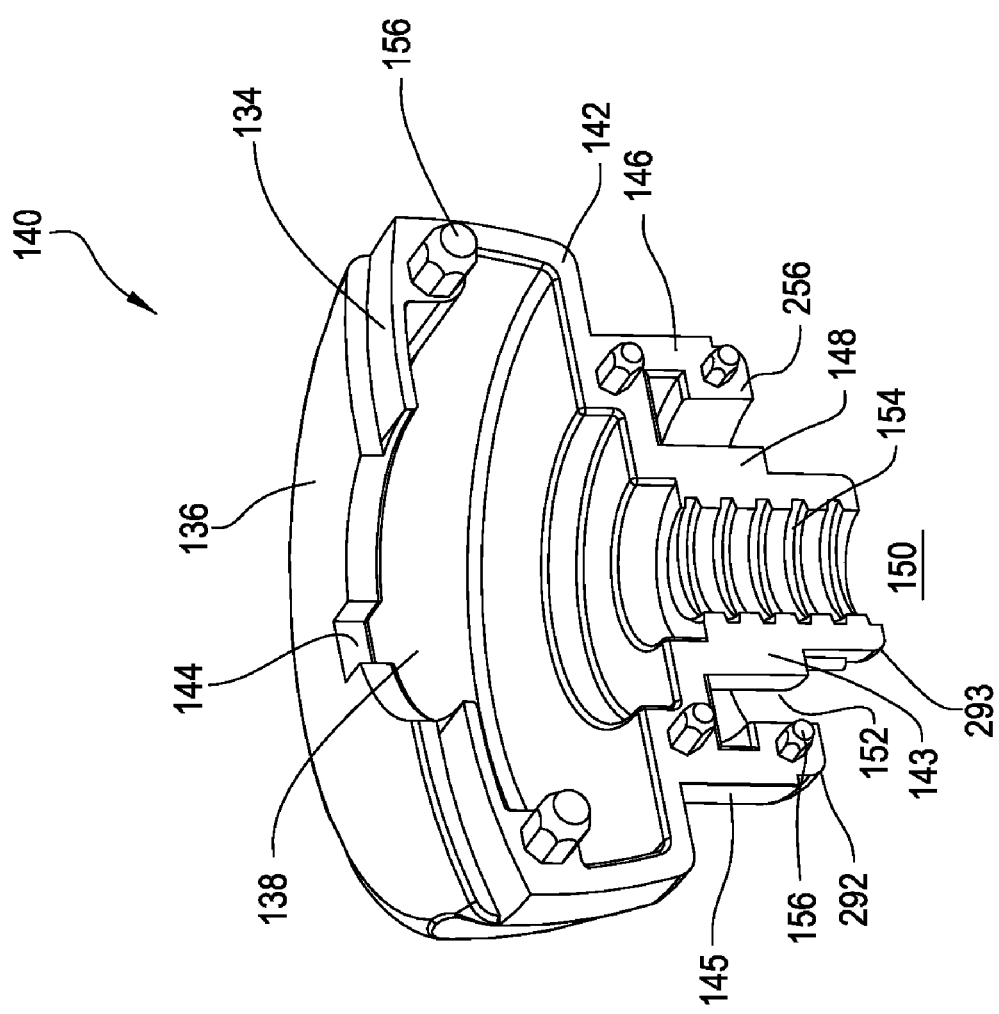
FIG. 18 is a perspective view of one (1) half of the knob in which the inner portion can be viewed.
Figure 19:
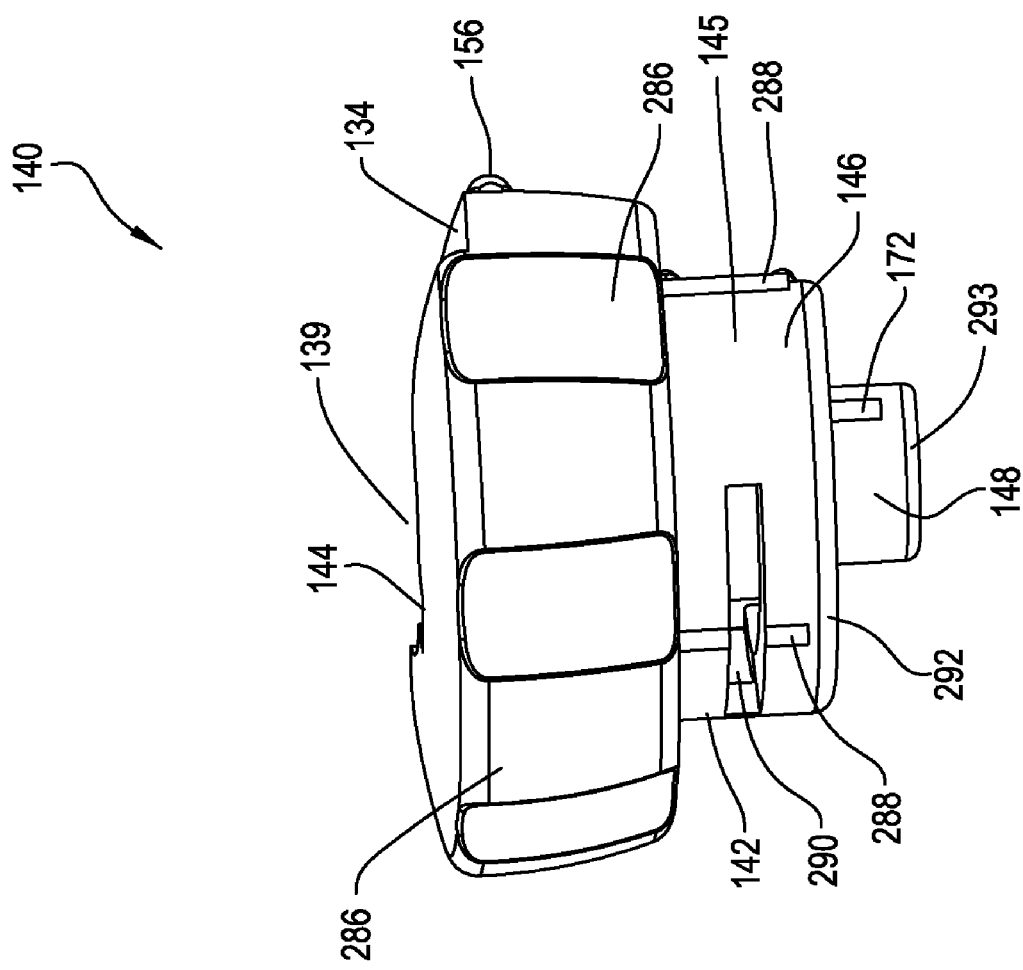
FIG. 19 is a perspective view of one (1) half of the knob in which the outer portion can be viewed.

FIGS. 16 and 17 are exploded and cross-sectional views, respectively, of the proximal end of cavity creator 100. Knob 140, best seen in FIGS. 18 and 19, is shaped to have a body 142 and two (2) downwardly extending rings 146, 148. The first ring 146 extends downward from the outer portion of the bottom surface of body 142. The second ring 148 extends downward from the center of the bottom surface of body 142 and forms bore 150. First ring 146 is outward of second ring 148, which are separated by gap 152.

Second ring 148 comprises two (2) sections (not identified). The first section is proximate to knob body 142. The second section is below the first section and has a smaller diameter than the first section. The two (2) sections define a step 143 therebetween. The second section, it should be understood, has a diameter slightly less than the distance between handle steps 108.

Bore 150 of second ring 148 is formed to have threading 154 on its inner surface. Threading 252 on the outer surface of base 242 of luer hub 240 engages complementary threading 154. Luer hub 240 therefore converts the rotation of knob 140 to longitudinal displacement of cement cannula 200 to function as a drive member to extend and retract blade 210.

First ring 146 comprises inwardly extending lip 256. When cavity creator 100 is assembled, tabs 116 of handle 110 (see FIGS. 5 and 6) extend upward into gap 152. Lip 256 is disposed below the outwardly projecting lips 106 integral with handle tabs 116. The lip-under-lip arrangement allows knob 140 to rotate, but does not allow it to be upwardly removed from handle 110.

As can be seen in FIG. 16, knob 140 comprises two (2) matable halves. Referring now to FIG. 18, in which the male half of knob 140 is shown, the male half includes six (6) mating members 156. The female half (not shown) includes six (6) corresponding receiving members for engaging mating members 156. Mating members 156 and the corresponding receiving members are press fit together. It should be understood that the two (2) halves of knob 140 can alternately be secured to one another by a greater or lesser number of mating members 156 and receiving members, by heat, an adhesive, screws, or any combination thereof.

Referring to FIGS. 18 and 19, one half of circular opening 138 formed in the top of knob body 142 can be seen. Opening 138 is dimensioned to receive luer cap 260. Knob body 142 is further shaped to have notch 144 that extends radially outwardly from opening 138. Notch 144 is sized to allow luer cap tab 255 (see FIG. 21) to pass therethrough when properly aligned in order to remove stylet 230.

Also visible in FIGS. 18 and 19 is one half of slot 134. Each half of knob 140 includes one half of slot 134 such that when mated, the halves form slot 134. Slot 134 is formed as part of knob top surface 136 and that part of top surface 136 forming slot 134 has a thinner thickness as compared to the remaining portion of knob top surface 136. Slot 134 extends along the opposing inner facing mating surfaces of each half of knob 140 and extends from the outer edge of opening 138 to the outermost edge of knob 140. Slot is further oriented substantially perpendicular to notch 144. When assembled and handle cap 180 is positioned over handle 110, slot 134 receives rib 188 on the under surface of handle cap arms 186 (see FIG. 22). With ribs 188 positioned within slot 134, knob 140 cannot be rotated. Handle cap 180 therefore prevents rotation of knob 140.

With reference to FIG. 19, positioned on outer surface 145 of knob 140 are four (4) outwardly extending detents 288. Detents 288 are oriented along axes parallel to the longitudinally axis of cavity creator 100. In the drawings, not all four (4) detents 288 are visible. Specifically, in the embodiment shown, a first detent 288 (on the left of body 142) is positioned on outer surface 145 of knob 140. The other half of knob 140 has a similarly located detent 288. Detent 288 (located on the right of body 142) is only a half of a detent. The other half of knob 140 has a corresponding half detent 288 that, when the two (2) halves of knob 140 are mated, form a full detent 288. Similarly, each half further includes a second half detent 288 on the opposite mating side (not visible). The result is four (4) full detents 288. Detents 288 are all spaced apart from one another at approximately ninety degree (90°) increments.

Ribs 286 are also visible on the outside of body 142. Because the practitioner may be wearing gloves and/or have fluids on their hand, ribs 286 allow the practitioner to better grip knob 140. Knob 140 can have any number of ribs 286, and it is not intended that ribs 286 be limited to any width, depth, spacing between, or orientation. As an alternate gripping mechanism, knob 140 can further include studs, textured portion(s), an elastomeric material positioned on any portion or entirely around knob 140, or any combination thereof.

Also visible in FIGS. 18 and 19 are slot 290 and corners 292, 293. Slot 290 is formed in first ring 146 and extends circumferentially around an outer section of ring 146. Each half that forms knob 140 is formed with slot 290. Slots 290 are present for manufacturing reasons and are otherwise not relevant to this invention. Corners 292, 293 are rounded surfaces where each vertical surface meets the horizontal surfaces of rings 146, 148. The rounded surfaces are also not integral to the invention.

Knob second ring 148 is further formed to have a single outwardly extending rib 172 seen best in FIG. 19. Rib 172 is dimensioned to fit in handle grooves 127 and 128. More particularly, rib 172 has a radius of curvature that is less than the radius of curvature of groove 127. Knob 140 is further formed to have a single tab 235, seen in cross section in FIG. 17. Tab 235 extends radially outwardly from the distal end of knob first ring 146.

Figure 20:
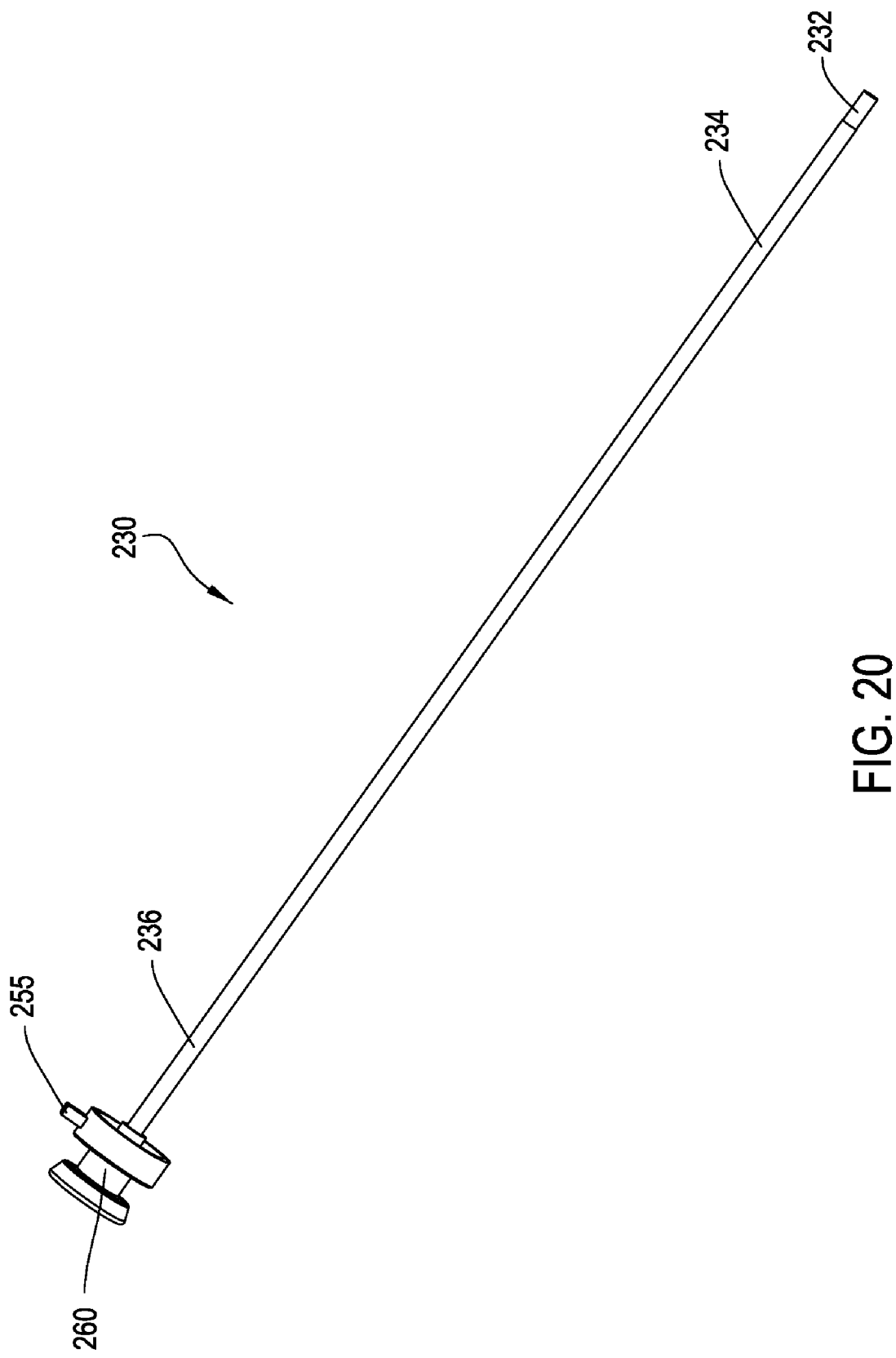
FIG. 20 is a perspective view of the stylet, including the luer cap.

FIG. 20 shows stylet 230, including luer cap 260. Stylet 230 is a substantially solid rod and comprises distal end 234 and proximal end 236. Stylet 230 has an outer diameter that allows stylet 230 to slip fit within cement cannula lumen 202. Luer cap 260 is fitted over and secured to proximal end 236 of stylet 230. Plug 232 is secured to distal end 234 of stylet 230 and made of a flexible material. Stylet 230 and plug 232 are collectively shaped so that plug 232 extends forward of cement cannula 200.

Stylet 230 is shaped so that the distal end of the stylet does not extend into tip 170. When stylet 230 is positioned within cement cannula 200, at least a portion of stylet plug 232 extends through tip bore 214 towards the access cannula discharge port 166. Stylet plug 232 does not extend out of the access cannula discharge port 166. This design feature substantially eliminates the possibility that, when the cavity creator 100 is inserted in the patient, tissue will catch in discharge ports 166 and 266. Stylet 230 is held in place by the frictional engagement between stylet plug 232 and bore 214 to prevent rotation of stylet 230. Because stylet plug 232 is made of a flexible material, it can be slid along lumen 202 of cement cannula 200 and bend off axis from the stylet 230 to extend into tip bore 214.

Stylet plug 232 is made of an elastomeric material such as that manufactured under the trademark Santoprene® by Advanced Elastomer Systems of Akron, Ohio but can be made of any other natural or man-made material having similar flexibility, durability, and biocompatibility characteristics, including silicone. Stylet 230 is made of 316 stainless steel, but can alternately be made of another sufficiently corrosion-resistant, biocompatible, and strong material, including but not limited to 420 stainless steel, 304 stainless steel, and 17-4 pre-hardened stainless steel. Luer cap 260 is made of the same material as handle 110, but can also be made of any material commonly known and used in the art having similar characteristics.

Figure 21:
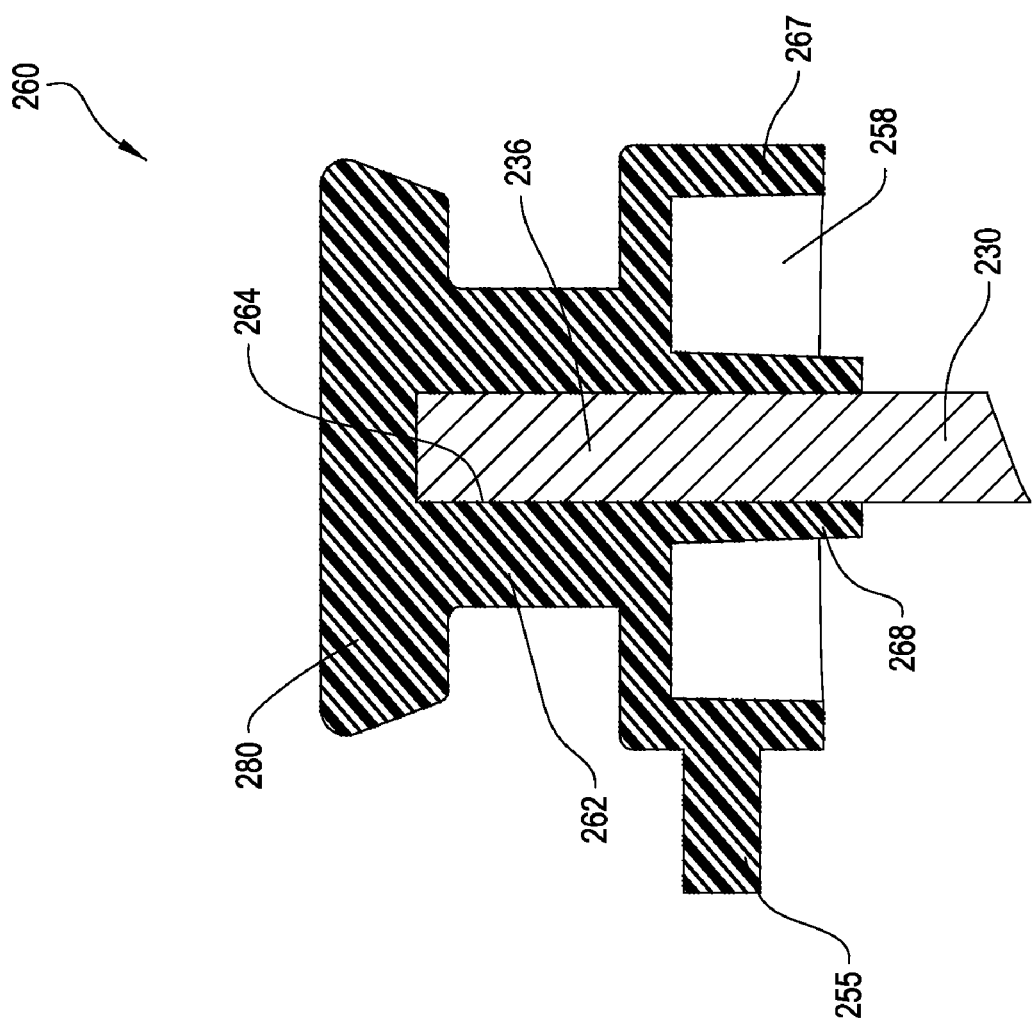
FIG. 21 is a cross-sectional view of the luer cap shown in FIG. 20.

Luer cap 260, as seen by reference to FIGS. 20 and 21, is generally cylindrical and comprises body 262, outer skirt 267, inner skirt 268, recess 258 between skirts 267, 268, tab 255, and luer boss 280. Body 262 is substantially cylindrical. Luer boss 280 is integrally formed with and positioned on the proximal end of luer body 262. Boss 280 is also substantially cylindrical in shape and extends outward from body 262. Luer boss 280 also extends upward beyond the top surface of knob 140 when stylet 230 is positioned within cavity creator 100. Luer boss 280 allows the practitioner to grasp luer cap 260.

At the distal end of luer body 262 are outer skirt 267 and inner skirt 268. Outer skirt 267 is positioned outward of luer body 262 to approximately the same diameter as luer boss 280 and extends downward from body 262. Inner skirt 268 extends downward from body 262 below outer skirt 267. Inner skirt 268 is further formed to have a tapered outer diameter that increases from the distal end of skirt 268.

Inner skirt 268, body 262, and a portion of boss 280 also form a generally cylindrical bore 264. Bore 264 is sized to receive proximal end 236 of stylet 230. Luer cap 260 is overmolded onto stylet 230.

Tab 255 extends radially outward from outer skirt 267 and prevents stylet 230 from being unintentionally removed from lumen 202. Specifically, in order to remove stylet 230, tab 255 must be aligned with notch 144 (see FIG. 18) in top surface 136 of knob 140.

Figure 22:
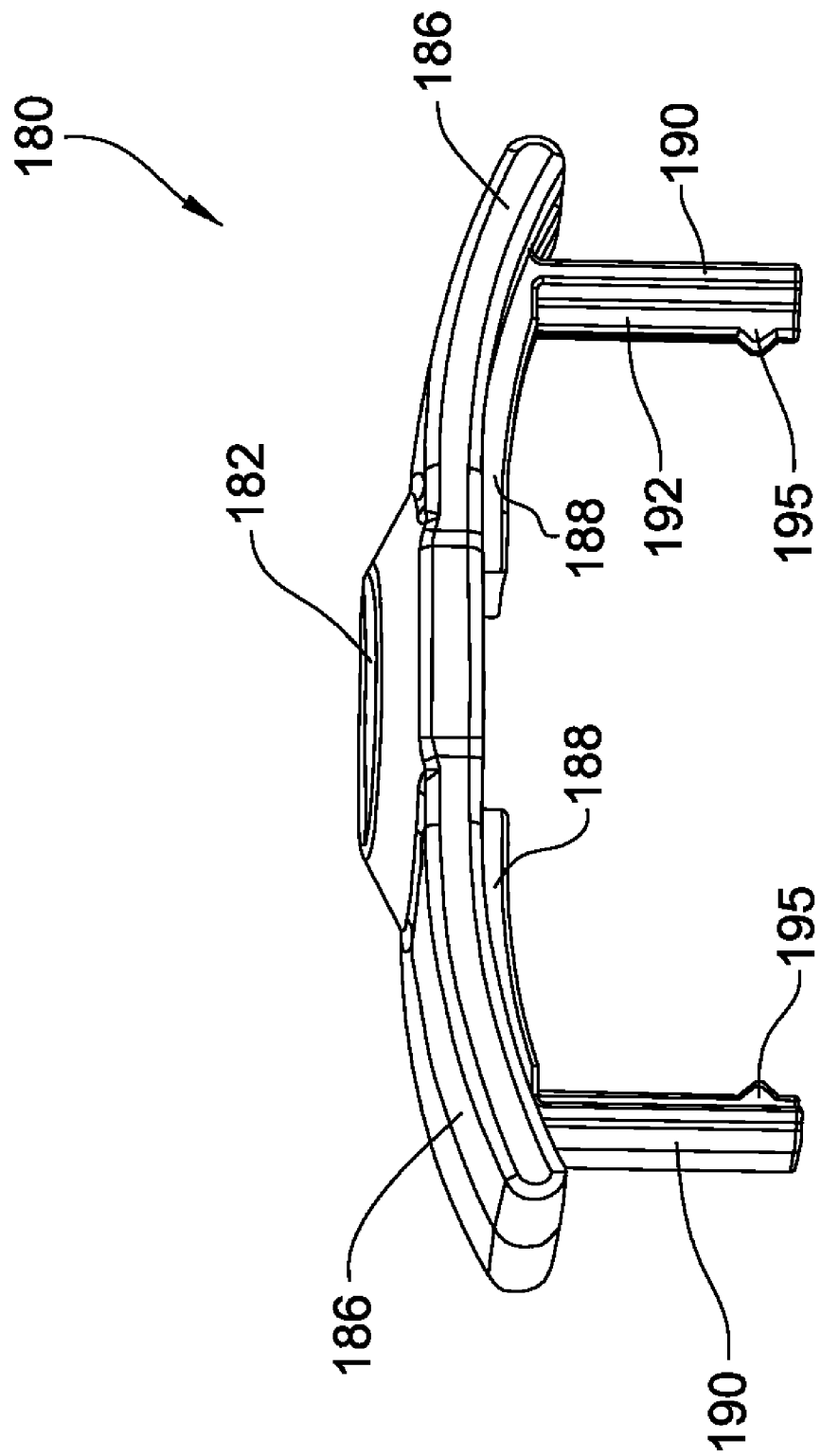
FIG. 22 is a perspective view of the handle cap.

FIG. 22 illustrates cap 180. Cap 180 can be made out of the same material from which handle 110 is formed. Cap 180 is formed as a single piece component shaped to have head 182 in form of a flat surfaced dome. As seen best in FIG. 17, the undersurface of head 182 is shaped to have cavity 184. Cavity 184 is dimensioned to receive the top of luer cap 260. Two arms 186 extend radially outwardly from the opposed sides of head 182. Each arm 186 is generally in the form of a bar that curves downwardly as arm 186 extends away from head 182. Extending downwardly from the undersurface of each arm 186 is rib 188. Ribs 188 have a side-to-side width less than arms 186 from which ribs 188 extend. Ribs 188 mate with slot 134 on top surface 136 of knob 140 to prevent rotation of knob 140 until knob cap 180 is removed.

Fingers 190 extend downwardly from the undersurface of each arm 186. Fingers 190 are located inwardly of the outer ends of each arm 186. Each rib 188 abuts the end of the associated finger 190. Fingers 190 are formed to have a T-shaped cross sectional profile such that each finger 190 has flange 192. Cap 180 is further shaped so that finger flanges 192 are directed inwardly, towards each other. Flanges 192 provide structural support for when cavity creator 100 is hit with an impact device. Knuckles 195 extend outwardly from each finger flange 192. Knuckles 195 are thus directed inward toward each other. Each knuckle 195 is in the shape of a triangle that has a notch that extends inwardly from the apex (notch not identified).

Cap 180 is further formed so that fingers 190 have widths that allow fingers 190 to seat in the opposed handle recesses 120. When cap 180 is so positioned, knuckles 195 seat in grooves 102 formed in handle 110. The seating of cap knuckles 195 in handle grooves 102 serves to releasably hold cap 180 to handle 110.

Also, handle cap 180 is shaped so that when handle cap 180 is seated over the rest of cavity creator 100, as seen in FIG. 17, there is first gap 174 between the top of luer cap 260 and the adjacent undersurface of cap head 182. There is also a smaller and outwardly directed second gap 176 between ribs 188 below each arm 186 and top surface 136 of knob 140.

In use, cavity creator 100 can be used by performing the following steps. It should be noted that not every step need be included in every procedure involving cavity creator 100 and that additional and/or equivalent steps can be included without departing from the spirit and scope of the invention.

Figure 25:
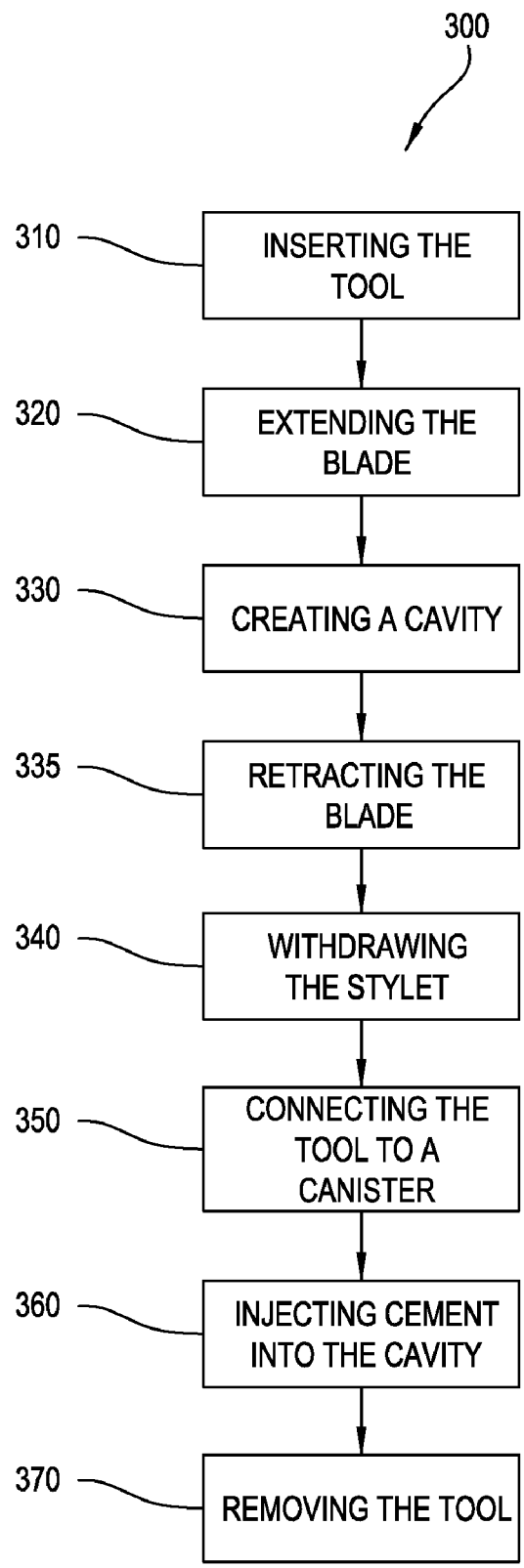
FIG. 25 is a flowchart representing one embodiment of a method of using the cavity creator.

FIG. 25 is a flowchart representing one (1) method 300 of using cavity creator 100 of the instant invention. In using cavity creator 100, the following steps can be performed: inserting the cavity creator 310, extending the blade 320, creating a cavity 330, retracting the blade 335, withdrawing the stylet 340, connecting the cavity creator to a canister 350, injecting cement or another material into the cavity through the cavity creator 360, and removing the cavity creator 370.

Upon assembly of cavity creator 100, a pair of opposed knob detents 288 are seated in handle finger grooves 126. Knob rib 172 is, at this time, seated in handle groove 127.

Step 310 comprises inserting cavity creator 100 into vertebra 55 or other bone tissue, whether additional tissue must be traversed (for example, through skin over vertebra 55) or vertebra 55 or other bone is exposed. Sometimes, prior to the actual insertion of cavity creator 100, a small incision is made to form an opening in the skin at which the cavity creator 100 is to be inserted.

The actual insertion is typically done by hand, but a hammer or other impact device can also be used to insert cavity creator 100. During this process the head of the hammer is brought down against cap head 182. The force of this impact is transferred through cap arms 186 and fingers 190 to handle 110. From handle 110, the force is transmitted through access cannula 160 to tip 170. It should further be appreciated that because cap head 182 is spaced above stylet cap 260 this impact force is not transferred to stylet 230. Thus, the driving of cannulas 160 and 200 into the bone does not result in the simultaneous further driving of stylet 230 out of access cannula discharge port 166. If a very large amount of impact energy is applied to cap 180, cap arms 186 will flex. Typically, the degree of arm flexure is such that the arms 186 do not contact and therefore do not transfer energy to the underlying surfaces of knob 140. This flexure thus substantially eliminates the likelihood that the application of energy to cap 180 will result in structural failure of cap 180 or the underlying knob 140.

During cavity creator insertion, it should be appreciated that blade 210 is in the retracted state, the longitudinal axis of the blade is at least parallel to, if not aligned with, the longitudinal axis of access cannula 160. Also, stylet tip 232 is disposed in tip bore 214. The presence of tip 232 in bore 214 during the insertion process reduces the likelihood that, during the insertion process, tissue will catch in the access cannula discharge port 166 or tip bore 214.

To extend the blade, step 320, handle cap 180 is first removed from the rest of cavity creator 100. The removal of cap 180 moves cap ribs 188 away from knob slot 134. This allows knob 140 to be rotated. Prior to the actual extension of blade 210, the practitioner may rotate cavity creator 100 so blade 210 will extend into the specific section of bone in which the cavity is to be formed. As a consequence of the extension of the blade 210, the longitudinal axis of the blade becomes angled relative to the longitudinal axis of the access cannula 160. Specifically, cavity creator 100 is rotated until the base of handle shoulder 113 points to the section of the bone into which the practitioner wants blade 210 to extend.

Blade 210 is extended by rotating knob 140. Upon initial rotation of knob 140, knob rib 172 rotates out of handle groove 127. Handle 110 is dimensioned such that during this displacement of knob 140, rib 172 does not abut the surface of handle 110 that defines groove 127. Accordingly, this displacement of rib 172 does not provide tactile feedback to the practitioner that knob 140 is being rotated. The initial rotation of handle 140 also simultaneously forces knob detents 288 out of handle grooves 126. The abutment of detents 288 against the groove-defining surfaces of handle 110 does provide a tactile feedback of knob 140 rotation.

Figure 23:
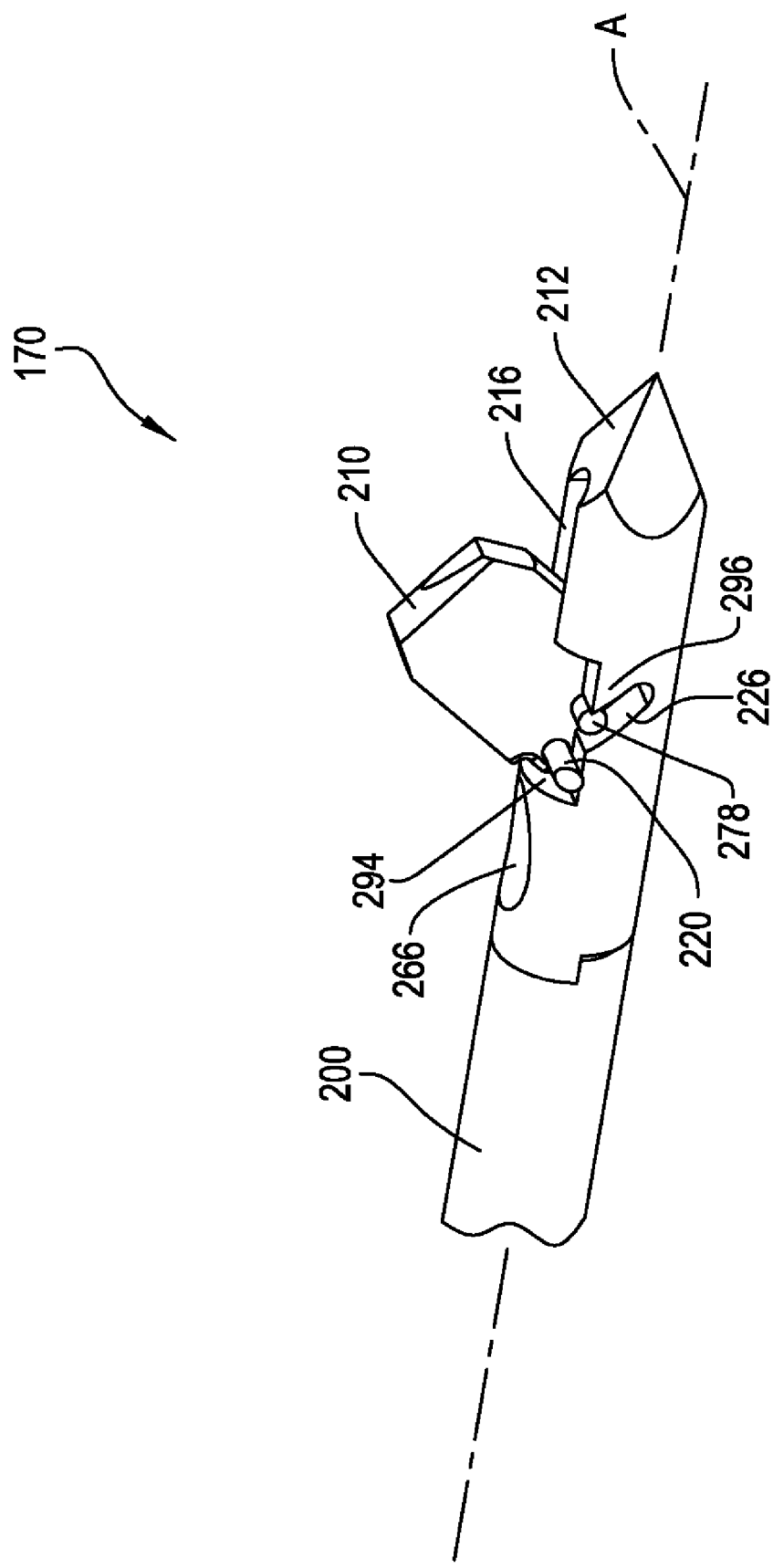
FIG. 23 is a perspective view of the cement cannula in which the blade is deployed.
Figure 24:
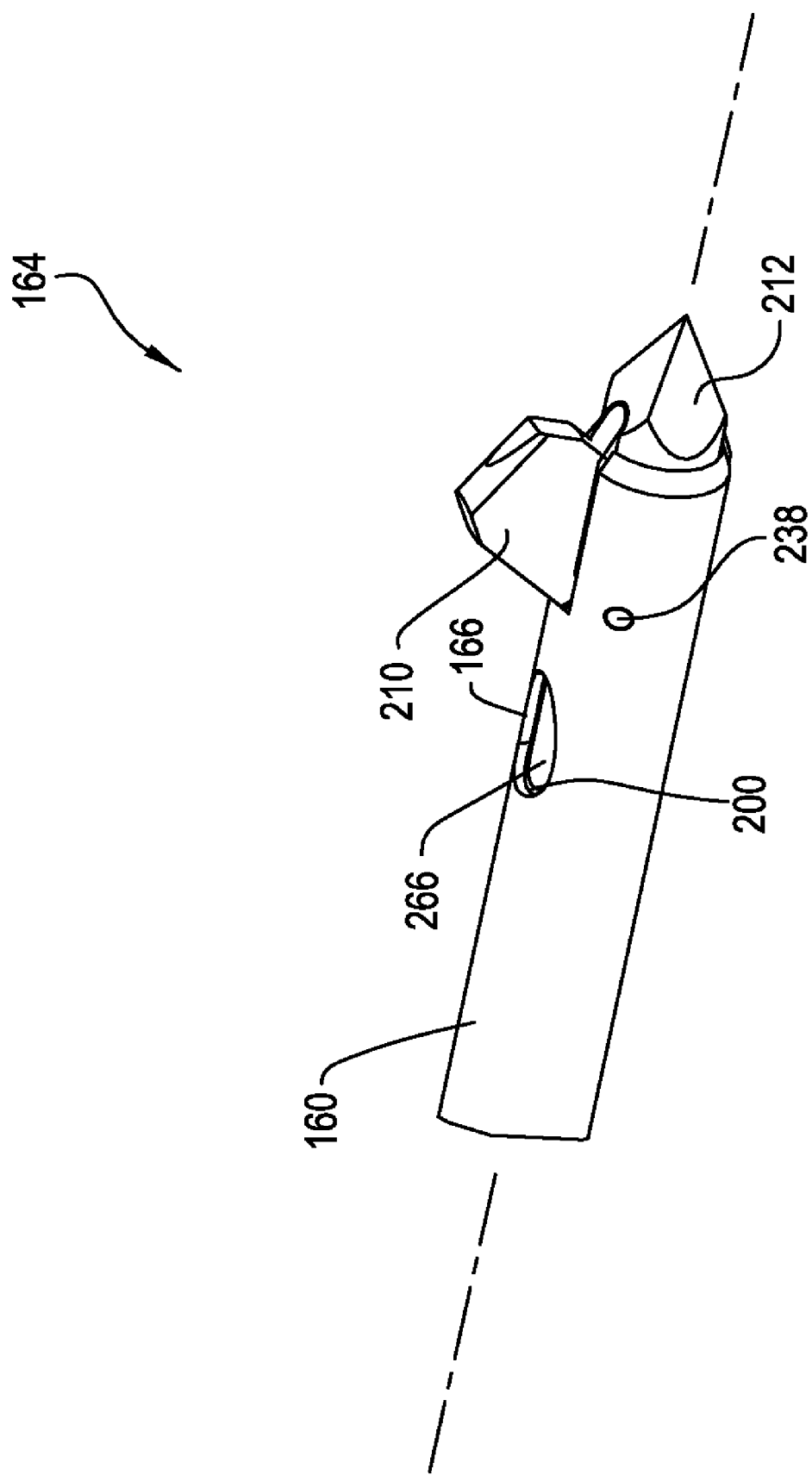
FIG. 24 is a perspective view of the distal end of the access cannula in which the blade is deployed.

When knob 140 is turned, the inner or cement cannula 200 longitudinally translates relative to the outer or access cannula 160. Pivot pin 220 is fixed relative to access cannula 160, and blade 210 is positioned within cannulas 160, 200. When cement cannula 200 and tip 170 are longitudinally translated forward, the rear surfaces of tip 170 that define slots 226 are pushed against posts 278 on blade 210, as seen in FIG. 23. This action pushes blade 210 outwardly so that blade 210 rotates around pivot pin 220 and extends out of one of the access cannula slots 159 as seen in FIG. 24.

The rotation of knob 140 also rotates knob notch 144 so that the notch moves out of registration with stylet cap tab 255. This new orientation of knob 140 relative to luer cap tab 255 places knob 140 in the position in which knob 140 blocks removal of luer cap tab 255 and therefore the whole of stylet 230, from the rest of cavity creator 100. During this process, since the stylet plug 232 is disposed in tip bore 214, the plug 232 is in an off axis position to stylet 230 itself. This off axis position of stylet plug 232 inhibits the manual rotation of stylet 230 that could place luer cap tab 255 in registration with knob notch 144. Thus, collectively, the inhibiting of the rotation of stylet 230 and the reorientation of knob 140 mean that when knob 140 is rotated to extend blade 210, stylet 230 is blocked from removal from the rest of the assembly.

By selectively rotating knob 140, the practitioner regulates the extent to which blade 210 projects away from access cannula 160. Detents 288 provide an indication of the extent to which knob 140 is rotated from the initial state so as to provide an indication of the degree of blade extension. Specifically, once knob 140 is rotated 90° from the initial state, a second pair of opposed detents 288 seat in handle grooves 126 to provide an indication of the quarter-turn rotation of knob 140. This means that the blade 210 is extended approximately one-quarter from its retracted state. The rotation of knob 140 180° results in the opposed pair of detents 288 that were initially seated in the handle grooves 126 reseat in the grooves. However, each detent 288 seats in a groove 126 opposite the groove 126 in which the detent 288 was initially seated. This seating of detents 288 provides tactile feedback that knob 140 has undergone a half turn of rotation. This should, in turn, be understood to mean that the blade 210 is approximately half way between the fully retracted and fully extended states. When knob 140 is rotated 270°, the second pair of opposed detents 288 again seat in handle grooves 126. The movement of detents 288 in and out of grooves 126 provides the indication that knob 140 has undergone more that a three-quarters turn rotation. It should therefore be understood that the blade 210 should be considered about three-quarters fully extended.

In the described version of the invention, knob 140 is not rotated a full 360°. Instead, the knob is able to rotate between typically between 330° and 350°. In some versions of the invention, the knob is able to rotate between 340° and 345°. When the knob 140 is fully rotated, the blade 210 fully extended, knob rib 172 seats in handle groove 128. The seating of rib 172 in groove 128 provides the tactile feedback that the knob is fully rotated. Should one try to force further rotation of knob 140, knob tab 235 abuts handle stop 130 to prevent such movement.

Figure 26A:
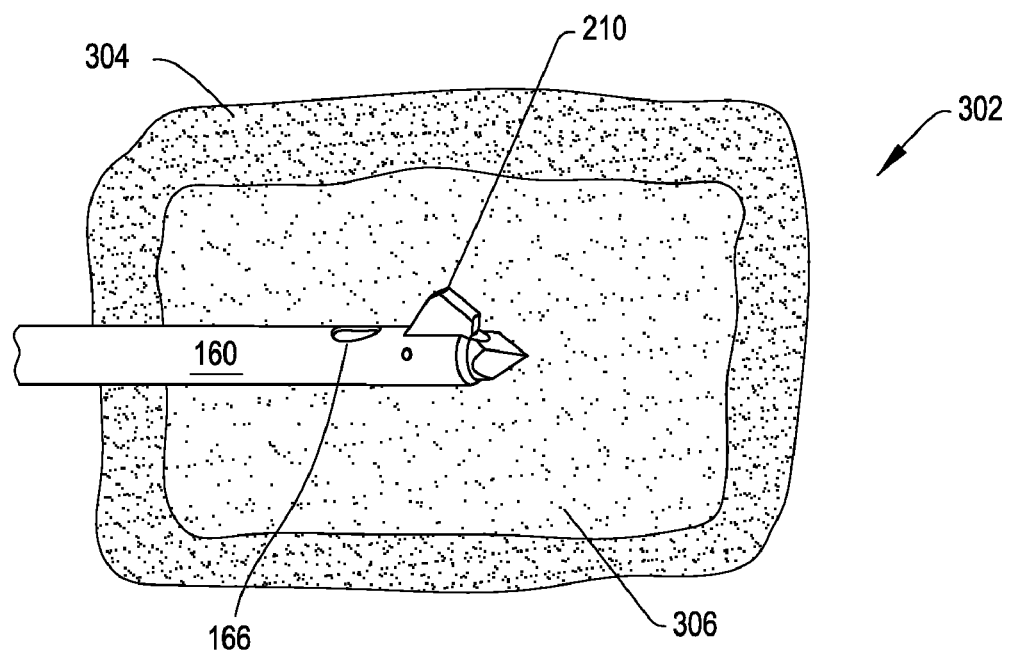
FIG. 26A is a cross sectional view of a bone where the cavity creator of this invention is in the bone forming a cavity.
Figure 26B:
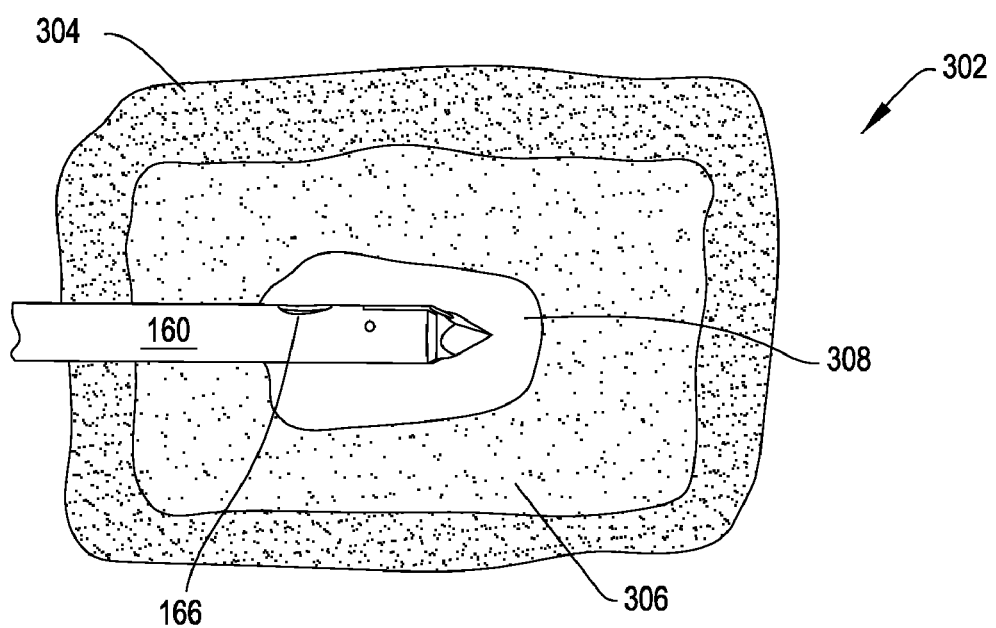
FIG. 26B is a cross sectional view of the bone after the cavity was created.

Once blade 210 is extended, the cavity is created in the bone, step 330. This step is performed by the practitioner rotating cavity creator 110. This rotation causes blade 210 to move against and scrape the porous cancellous tissue 306 that forms the center of the bone 302 as seen in FIG. 26A. In the Figures, the dense cortical tissue 304 that forms the outer shell of bone 302 is represented by dense stippling; the inner porous cancellous tissue 306 is represented by sparse stippling. As seen by FIG. 26B, the grinding of the cancellous tissue 306 forms a cavity 308 in the bone 302 where this tissue was previously located. Again, the practitioner is able to selectively control where in the bone 302 the cavity 308 is created by regulating the arc through which blade 210 is rotated. The practitioner monitors blade position by monitoring the location of the distally directed base of the handle shoulder 113. During this process, cavity creator 100 can be displaced longitudinally. This allows the practitioner to set the length of the cavity 308. Likewise, it should be appreciated that the practitioner may chose to first partially extend the blade and create a small cavity. Once this small cavity is created the practitioner may then more fully extend the blade 210 to create a larger cavity.

Cavity creator 100 can be completely rotated to form a 360° cavity around cavity creator 100 or can be rotated to an extent less than complete rotation to create a cavity only around a portion of cavity creator 100. Cavity creator 100 can, while being rotated, also be moved longitudinally to create a cavity that is longer than the length of blade 210.

During the cavity creation process, stylet plug 232 is disposed is disposed in tip bore 214. Plug 232 prevents tip bore 214 and cement cannula lumen 202 from clogging, which could inhibit the subsequent delivery of cement. Also, while blade 210 is extended, owing to the forward longitudinal displacement of the cement cannula 200 and tip 170 relative to the access cannula 160, tip discharge port 266 moves out of registration with the access cannula discharge port 166. More particularly, the section of the tip 170 proximal to discharge port 266 moves under the access cannula discharge port 166. This further blocks the flow of material into tip bore 214 and cement lumen 202.

Once the cavity is created, blade 210 is retracted, step 335, by reversely rotating knob 140. The rotation of knob 140 causes cement cannula 200 to retract proximally rearward. This results in blade pins 278 being pressed against the surfaces of tip 170 that define the distal ends of slots 226. The pressing of the blade pins 278 against these surfaces rotates blade 210 about pivot pin 220 to the retracted position. As a consequence of this rotation of knob 140, knob notch 144 is rotated back into alignment with luer cap tab 255. Thus, at this time stylet 230 can be removed from cavity creator 100, step 340.

It should further be appreciated that the retraction of the cement cannula 200 proximally rearward places the tip discharge port 266 back into registration with the access cannula discharge port 166.

Step 350 comprises connecting cavity creator 100 to cartridge 40. Bone cement or other filler material to be injected into the cavity is contained in cartridge 40. Cartridge 40 is mechanically connected to cavity creator 100 by flexible tubing 42 or other appropriate means. As shown herein, flexible tubing 42 is connected to cavity creator 100 by a threaded fitting (not shown) on flexible tubing 42 that mates with threading 254 on luer hub 240.

Figure 26C:
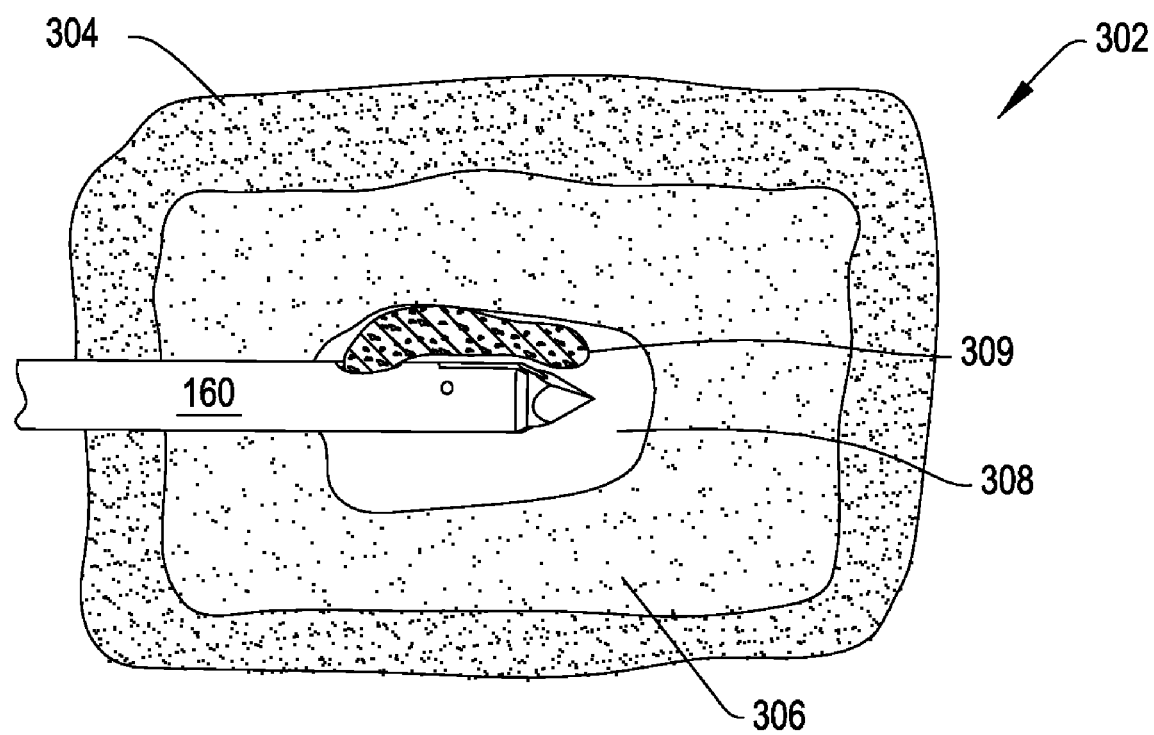
FIG. 26C is a cross sectional view of the bone wherein a plume of cement is discharged from the cavity creator into the cavity.

Step 360 comprises injecting the bone cement or other filler material into to the cavity. The material is ejected from cartridge 40 using plunger 44, but can be ejected using any other mechanism or device. The ejected material passes through flexible tubing 42, through lumen 202, cement cannula discharge port 266 and access cannula discharge port 166 into the cavity 308 as seen in FIG. 26C. In FIG. 26C a plume of cement 309 is seen discharged from the access cannula port 166 into the cavity 308. The mass of cement fixates fractures present in the bone. The injection of other filler material into the bone cavity provides the same and/or other therapeutic benefit.

The present invention is not limited to the particular material being injected or the type of bone into which the material is being injected. Such a procedure allows the practitioner to control the time at which the material being injected (that is, early in the curing process in which the material is less viscous or later in the curing process in which the material is more viscous), the volume of the material being injected, as well as the pressure at which the material is injected.

Step 370 comprises removing cavity creator 100 from the patient. That is, once the material has been injected into the cavity, cavity creator 100 is extracted from the bone and any other tissue that cavity creator 100 passed through to get to the bone.

It should be appreciated that a feature of this invention therefore is that it provides a single device for: penetrating the bone; forming the cavity in the bone; and functioning as the delivery conduit through which the filler material can then be introduced into the cavity. The need to use plural instruments to perform these steps is therefore eliminated. Eliminating the need to position plural instruments in the bone both minimizes the complexity of the procedure and the overall amount of time it takes to perform the procedure.

With respect to the method shown and described herein, it should be understood that the steps need not be performed in any particular order. For example, step 350 of connecting cavity creator 100 to cartridge 40 can be performed between or during other steps of method 300.

While cavity creator 100 and method of using same has been shown and described primarily with respect to one (1) specific version, from the above description it should be clear that the same is not limited thereto, but is susceptible to numerous changes and modifications as known to a person of ordinary skill in the art. There is no requirement that all versions of the invention include each of the above-described features. For example, cavity creator 100 need not include handle cap 180. As a further example, knob 140 need not have ribs 286 or another means for helping the practitioner grasp cavity creator 100. In addition, threading 254 on luer hub head 244 is only one way by which delivery tube 42 can be attached to cement cannula 200. For example, in one alternate version, delivery tube 42 frictionally engages luer hub 240 such that threading 254 is unnecessary. In some versions of the invention, the pivot pin 220 may be welded to the access cannula 160.

Likewise, it may not be necessary in some versions of the invention to provide the stylet 230 with a flexible plug that extends towards the tip discharge port 266.

Figure 28:
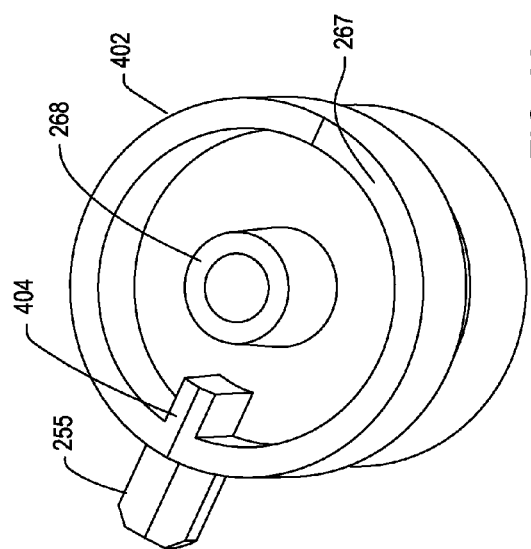
FIG. 28 is a perspective view of the underside of an alternative stylet cap of this invention.
Figure 27:
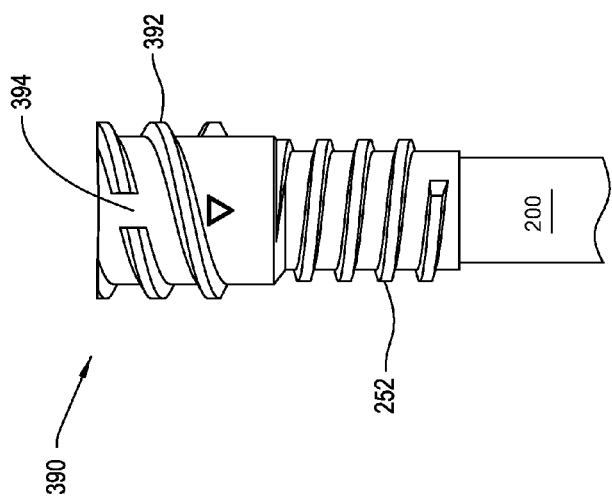
FIG. 27 is a side view of an alternative luer hub of this invention.

In versions of the invention in which the stylet is not provided with a plug or in other versions of the invention, alternative means may be provided to prevent removal of the stylet 230 when the blade 210 is in the extended state. For example in one alternative version of the invention, an alternative luer hub 390 seen in FIG. 27 is disposed over the proximal end of the cement cannula 200. Luer hub 390 has the same basic features as luer hub 240. Luer hub 390 is further formed so that the top most threading 392 that receives the luer fitting is formed to have a break 394. This version of the invention includes a stylet cap 402, partially seen in FIG. 28. Stylet cap 402 includes the same basic features of stylet cap 260. Stylet cap 402 is further formed so that extending inwardly from the inner surface of outer skirt 267 there is finger 404. In the illustrated version of the invention the longitudinal axes of tab 255 and skirt finger 404 are coaxial. The side-to-side width of finger 404 is less than the side-to-side width of tab 255.

Figure 29:
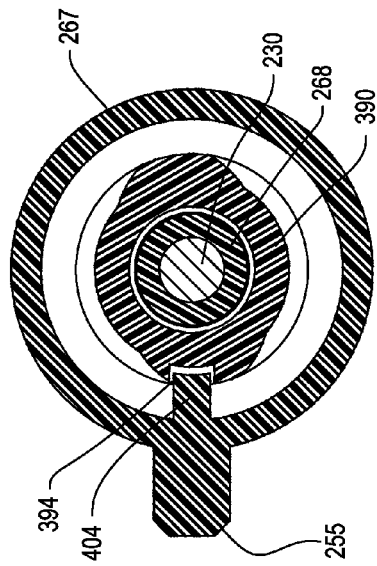
FIG. 29 is a cross sectional view of how the stylet cap of FIG. 28 engages the luer hub of FIG. 27.

As seen in FIG. 29, in this version of the invention, when stylet cap 402 seats over luer hub 390, cap finger 404 seats in the luer hub break 394. The finger-in-break engagement of the hub 390 and cap 402 prevents the stylet cap from rotating relative to the luer hub. When the knob 140 is rotated to extend the blade 210, cement cannula 200 only undergoes translation motion, the cannula 200 does not rotate. Again such rotation causes the knob notch 144 to rotate out of registration with cap tab 255. Owing to the seating of the stylet cap finger 404 in fitting break 394, the stylet cap 402 cannot be rotated to place the cap tab 255 in registration with knob notch 144. As with the first described version of the invention, since the cap tab 255 cannot be placed in registration with the notch 144, removal of the stylet 230 from the rest of the cavity creator is blocked.

In addition, alternate versions and geometries of the described features of the present invention are possible. Thus, alternate versions of cavity creator 100 may vary from what has been illustrated. For example, in the described version of the present invention, blade 210 has been shown as having a substantially rectangular cross-sectional shape. In alternate embodiments of the invention, blade 210 may be triangular, hooked, or have almost any other shape depending on the specific size and shape of the cavity to be created. In addition, head 212 has been shown as having four facets to form a generally pyramid shape. In still other embodiments of the present invention, head 212 can have any alternate shape that still allows cavity creator 100 to be inserted into the bone in which the cavity is to be formed. As a further example, handle 110 can have any shape that provides the practitioner the ability to grasp cavity creator 100. As still another example, access cannula 160 and tip 170 can be formed as one integrated element.

In some embodiments of the invention, the slots 224 in which blade pins 278 do not extend completely through tip 170. In these versions of the invention, the slots stop short of the outer circumferential wall of pin 170. Adjacent each slot there is a small web. One side of the web defines a portion of the outer circumferential surface of the tip 170; the opposed surface defines the end of the associated slot. In these versions of the invention, the webs add strength to the tip when it is inserted into tissue or the cavity creator 100 is rotated.

Likewise, cavity creator 100 of this invention may be used with cement or filler delivery devices other than the disclosed cartridge 40. For example in some versions of the invention, once the cavity creator is in place, a tube shaped cartridge may be disposed in the access cannula lumen. This cartridge is preloaded with cement or filler. Once this cartridge is in place, a plunger drives the cement from the cartridge into tip bore 214 and discharge ports 266 and 166.

From the above it should also be clear that bone filler other than cement may be supplied to the cavity created using the assembly of this invention. Other potential bone fillers than cement include: bone graft material or bone growth material. Likewise, the fillers that can be delivered using this invention are not limited to liquids and semi-solids. Solid implants like beads or other rigid fillers may be added using the assembly of this invention.

Similarly, other assemblies may be used to extend and retract the blade 210. For example in some versions of the invention, instead of using a threaded assembly to extend/retract the cement cannula 200 relative to the access cannula 160 a tab may be attached to the cement cannula 200. In this version of the invention, the practitioner slides the tab to cause displacement of the cement cannula in order to cause the desired extension/retraction of the blade 210. For example, an elongated rod may be slidably mounted to the access cannula 160. A rack of gear teeth engage complementary teeth associated with the blade. The rod is extended/retracted in order to cause a similar displacement of the blade 210. An advantage of this version of the invention is that the need to provide a moveable cement cannula is eliminated. Alternatively a cable with ends that are extended or retracted may be used to extend/retract the blade 210.

It should similarly be appreciated that other mechanisms may be employed to prevent removal of the stylet when the blade is in the extended state. For example the cement cannula may be provided with a finger that is biased to press into a notch in the stylet when the cement cannula is displaced in the forward direction. The seating of the finger in the notch blocks removal of the stylet. When the cement cannula is retracted proximally, the finger retracts from the stylet to allow removal of the stylet.

Likewise, in some versions of the invention, the access cannula may not have a lumen. In these versions of the invention, it should be appreciated that once the cavity is created, this invention is removed and a separate delivery cannula is used as the member for introducing filler material into the created cavity.

Furthermore, it should be understood that the materials and the method from which the various components of cavity creator 100 are formed should not limit the scope of this invention. Thus, it is intended that the appended claims not be limited to the details shown and described herein, but rather cover all such variations and modifications that come within the true spirit and scope of this invention.

What is claimed is:

1. A device for injecting cement into tissue, said device comprising:
    an access cannula having a lumen that extends along a longitudinal axis of said access cannula, opposed proximal and distal ends, and a discharge port that opens from said lumen adjacent the distal end of said access cannula;
    a stylet removably positioned within said access cannula lumen, said stylet having opposed proximal and distal ends, said stylet dimensioned so that when said stylet is in said access cannula lumen, said distal end of said stylet at least partially blocks said access cannula discharge port;
    a fitting adjacent the proximal end of said access cannula for receiving a delivery device from which cement is injected into the access cannula lumen for discharge through the discharge port;
    a blade movably attached to the distal end of said access cannula so as to move between a retracted position in which said blade is proximal to the longitudinal axis of said access cannula and an extended position in which said blade extends from the longitudinal axis of said access cannula;
    a drive member that extends through said access cannula, said drive member being movable within said access cannula and connected to said blade for moving said blade between the retracted and extended positions;
    an actuator movably mounted to said access cannula and attached to said drive member for moving said drive member; and
    a tip that extends forward from said distal end of said access cannula, said tip configured to penetrate tissue.

2. The device of claim 1, wherein said drive member is disposed in the access cannula lumen.

3. The device of claim 1, wherein said drive member is positioned in the access cannula lumen and has a section that, when said drive member is moved to move said blade from the retracted position, at least partially blocks the access cannula discharge port.

4. The device of claim 1, wherein said drive member further includes at least one inclined surface that abuts a section of said blade so as to move said blade between the extended and retracted positions.

5. The device of claim 1, wherein said drive member is a cement cannula that is moveably disposed in said access cannula lumen, said cement cannula comprising:
    a proximal end; a distal end positioned to engage said blade so as to move said blade between the retracted and extended positions; a lumen that extends forward from said proximal end; and a discharge port that opens from said lumen adjacent said distal end; and said fitting is connected to said cement cannula so as to establish a flow path for said cement into said cement cannula lumen.

6. The device of claim 5, wherein:

when said blade moves from the retracted position to the extended position, said blade moves outwardly from a side of the access cannula; and said access cannula and said cement cannula are shaped so that the discharge ports integral with said cannulae are located on the same side of the access cannula from which said bade outwardly moves.

7. The device of claim 6, wherein the discharge port of said access cannula opens within a maximum distance of 0.25 inches from a distal end of said tip.

8. The device of claim 1, wherein said tip and said drive member are separate components.

9. The device of claim 1, wherein said actuator has a locking component and said stylet has a locking component, said actuator and said stylet locking components configured to engage when said actuator is moved to extend said blade from the retracted position so that, when said blade is moved towards the extended position, said locking components prevent removal of said stylet from said access cannula.

10. The device of claim 9, wherein:

when said blade moves from the retracted position to the extended position, said blade moves outwardly from a side of the access cannula;

said access cannula and said cement cannula are shaped so that the discharge ports integral with said cannulae are located on the same side of the access cannula from which said bade outwardly moves; and the discharge port of said access cannula opens within a maximum distance of 0.25 inches from a distal end of said tip.

11. The device of claim 1, wherein said device further includes a cap removably attached to a proximal end of said device and spaced above and away from a proximal end of said drive member.

12. The device of claim 1, wherein:

said drive member is longitudinally displaced in the access cannula to move said blade between the retracted and extended positions; and said actuator is rotated to longitudinally displace said drive member.

13. The device of claim 1, wherein said actuator includes an indicator that provides an indication of the extent to which said blade is moved from the retracted position to the extended position.

14. The device of claim 1, wherein the discharge port of said access cannula opens within a maximum distance of 0.25 inches from a distal end of said tip.

15. A device for injecting cement into tissue, said device comprising:

an access cannula having a lumen that extends along a longitudinal axis of said access cannula, opposed proximal and distal ends, a discharge port that opens from the lumen adjacent the distal end of said access cannula, and is adapted to connect to a delivery device from which cement is injected into said access cannula lumen for discharge through the discharge port;

a blade pivotally attached to the distal end of said access cannula so as to move between a retracted position in which said blade is located proximal to the access cannula longitudinal axis and an extended position in which said blade extends away from the access cannula longitudinal axis;

a cement cannula disposed in the access cannula lumen and that is movable relative to said access cannula, said cement cannula comprised of: a proximal end; a distal end positioned to engage said blade so as to move said blade between the retracted and extended positions; a lumen that extends forward from the proximal end; and a discharge port that opens from the lumen adjacent the distal end;

an actuator movably mounted to said proximal end of said access cannula and attached to said cement cannula for moving said cement cannula so that the movement of said cement cannula results in the movement of said blade between the retracted and extended positions; and a tip that extends forward from said distal end of said access cannula, said tip configured to penetrate tissue.

16. The device of claim 15, wherein said cement cannula further comprises a section that, when said cement cannula is moved to move said blade from the retracted position to the extended position, at least partially blocks the access cannula discharge port.

17. The device of claim 15, wherein said access cannula further includes a slot in which said blade is seated when in the retracted position.

18. The device of claim 15, wherein said access cannula and said cement cannula are positioned so that:

when said cement cannula is positioned so that said blade is in the retracted position, said cement cannula discharge port is substantially in registration with said access cannula discharge port; and when said cement cannula is moved so as to move said blade from the retracted position, the cement cannula discharge port moves out of registration with the access cannula discharge port.

19. The device of claim 18, wherein said device further includes a stylet removably positioned within the cement cannula lumen, said stylet having opposed proximal and distal ends, said stylet dimensioned so that when said stylet is in the cement cannula lumen, said distal end of said stylet at least partially blocks said access cannula discharge port.

20. The device of claim 18, wherein the discharge port of said cement cannula opens within a maximum distance of 0.25 inches from a distal end of said tip.

21. The device of claim 18, wherein:

when said blade moves from the retracted position to the extended position, said blade moves outwardly from a side of the access cannula;

said access cannula and said cement cannula are shaped so that the discharge ports integral with said cannulae are located on the same side of the access cannula from which said bade outwardly moves; and the discharge port of said cement cannula opens within a maximum distance of 0.25 inches from a distal end of said tip.

22. The device of claim 15, wherein said tip is attached to said cement cannula so as to extend forward from said access cannula.

23. The device of claim 15, wherein said actuator is rotated to longitudinally displace said cement cannula.

24. The device of claim 15, wherein the discharge port of said access cannula opens within a maximum distance of 0.25 inches from a distal end of said tip.

25. A device for delivering bone filler material into tissue, said device comprising:
- an access cannula having a proximal end and a distal end, a longitudinal axis, and a lumen extending along the longitudinal axis;
- a blade pivotally attached to said distal end of said access cannula so as to move between a retracted position and an extended position;
- a cement cannula slidably disposed in said access cannula lumen, said cement cannula adapted to be connected to a delivery device containing said bone filler material and longitudinally translatable within said access cannula, said cement cannula having: a proximal end; a distal end positioned to engage said blade so as to move said blade between the retracted and extended positions; a lumen that extends forward from said proximal end; and a discharge port that opens from said lumen adjacent the distal end of said cement cannula;
- an actuator mounted to said proximal end of said access cannula and attached to said cement cannula for moving said cement cannula; and
- a tip attached to and extending forward from said distal end of said access cannula to move with said cement cannula, said tip configured to penetrate tissue.

26. The device of claim 25, wherein the access cannula discharge port opens from a side surface of said access cannula, the cement cannula lumen opens from a side surface of said cement cannula, and the access cannula discharge port and the cement cannula discharge port are positioned so that:
- when said cement cannula is positioned so that said blade is in the retracted position, the cement cannula discharge port is substantially in registration with said access cannula discharge port; and
- when said cement cannula is moved so as to move said blade from the retracted position, the cement cannula discharge port moves out of registration with said access cannula discharge port.

27. The device of claim 25, wherein said device further includes a cap removably attached to the proximal end of said access cannula and spaced above and away from said the proximal end of said cement cannula.

28. The device of claim 25, wherein the discharge port of said cement cannula opens within a maximum distance of 0.25 inches from a distal end of said tip.

* * * * *